(12) United States Patent
Vijendra et al.

(10) Patent No.: US 9,275,059 B1
(45) Date of Patent: Mar. 1, 2016

(54) GENOME BIG DATA INDEXING

(75) Inventors: Sudhir Vijendra, Cambridge, MA (US); Patricia G. S. Florissi, Briarcliff Manor, NY (US)

(73) Assignee: EMC Corporation, Hopkinton, MA (US)

( * ) Notice: Subject to any disclaimer, the term of this patent is extended or adjusted under 35 U.S.C. 154(b) by 0 days.

(21) Appl. No.: 13/290,858

(22) Filed: Nov. 7, 2011

(51) Int. Cl.
   *G06F 7/00* (2006.01)
   *G06F 17/30* (2006.01)

(52) U.S. Cl.
   CPC .................. *G06F 17/30067* (2013.01)

(58) Field of Classification Search
   CPC ................................ G06F 17/30067
   USPC ......................................... 707/802
   See application file for complete search history.

(56) References Cited

U.S. PATENT DOCUMENTS

| | | | | |
|---|---|---|---|---|
| 6,035,303 | A * | 3/2000 | Baer | G06F 17/30607 |
| 6,081,883 | A * | 6/2000 | Popelka | G06F 17/30067 707/E17.01 |
| 6,332,040 | B1 * | 12/2001 | Jones | G06F 17/30271 382/187 |
| 6,507,843 | B1 * | 1/2003 | Dong | G06K 9/6217 |
| 6,611,609 | B1 * | 8/2003 | Zhu | G06F 17/30244 345/589 |
| 7,548,928 | B1 * | 6/2009 | Dean | G06F 17/30985 |
| 7,739,311 | B2 * | 6/2010 | Smith | G06K 9/6253 707/802 |
| 8,185,551 | B2 * | 5/2012 | Kuszmaul | G06F 11/1471 707/705 |
| 8,615,481 | B1 * | 12/2013 | Pragada et al. | 706/50 |
| 9,031,992 | B1 * | 5/2015 | Florissi | G06F 19/321 707/794 |
| 2004/0024779 | A1 * | 2/2004 | Perry | G06F 17/30961 |
| 2004/0133583 | A1 * | 7/2004 | Tingey | G06Q 40/02 |
| 2005/0097127 | A1 * | 5/2005 | Foley | G06T 1/60 |
| 2005/0108203 | A1 * | 5/2005 | Tang et al. | 707/3 |
| 2008/0262660 | A1 * | 10/2008 | Weber | G06F 17/3087 701/1 |
| 2010/0318567 | A1 * | 12/2010 | Kuo et al. | 707/780 |
| 2011/0087854 | A1 * | 4/2011 | Rushworth | G06F 12/023 711/170 |
| 2011/0196602 | A1 * | 8/2011 | Pfeifle | G01C 21/3605 701/532 |
| 2011/0246503 | A1 * | 10/2011 | Bender et al. | 707/769 |
| 2011/0307436 | A1 * | 12/2011 | Cai | G06F 17/30864 706/48 |
| 2012/0173590 | A1 * | 7/2012 | Li | G06F 17/30587 707/803 |
| 2013/0110872 | A1 * | 5/2013 | Barga | G06F 17/30389 707/771 |
| 2013/0117272 | A1 * | 5/2013 | Barga | G06F 17/30551 707/741 |

\* cited by examiner

*Primary Examiner* — Eliyah S Harper
(74) *Attorney, Agent, or Firm* — Krishnendu Gupta; Joseph D'Angelo

(57) ABSTRACT

A computer implemented method, computer program product, and apparatus for modeling a Big Data dataset, the method comprising creating non-specific representations of the Big Data dataset by representing, as objects in a computer model, non-specific representations including metaInformation, DataSet, BigData and Properties representations and creating non-specific representations of indices, wherein the indices are mapped to one or more key-value pairs.

21 Claims, 27 Drawing Sheets

| Metric 2005 | DRAM 2010 | NAND Flash 2020 | HDD 2030 |
|---|---|---|---|
| IOPS 2040 | 500,000 | 5,000 | 250 to 500 |
| Bandwidth 2050 | 3,200 MB/s | 100 Mb/s for W 200 MB/s for R | 60 – 90 MB/s |
| Latency 2060 | 0.005 microseconds | 300 microseconds | 7 – 12 milliseconds |

Figure 20

File1: CAT 2310    File2: GAT 2320
FILE3: TAC 2340

| Sequence Size 2350 | Key 2360 | Value 2370 |
|---|---|---|
| 1 | C,1 | CAT |
|  | G,1 | GAT |
|  | T,1 | TAC |
|  | A,2 | CAT,GAT,TAC |
|  | T,3 | CAT,GAT |
|  | C,3 | TAC |
| 2 | CA,1 | CAT |
|  | GA,1 | GAT |
|  | TA,1 | TAC |
|  | AT,2 | CAT, GAT |
|  | AC,2 | TAC |
| 3 | CAT,1 | CAT |
|  | GAT,1 | GAT |
|  | TAC,1 | TAC |

Figure 23

GENOME BIG DATA INDEXING

RELATED APPLICATIONS

This application is related to co-pending U.S. patent application, filed even date, Ser. No. 13/290,838 entitled "META FILE SYSTEM FOR BIG DATA," which is hereby incorporated by reference in its entirety.

A portion of the disclosure of this patent document may contain command formats and other computer language listings, all of which are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to Big Data.

BACKGROUND

The amount of data in our world has been exploding. Companies capture trillions of bytes of information about their customers, suppliers, and operations, and millions of networked sensors are being embedded in the physical world in devices such as mobile phones and automobiles, sensing, creating, and communicating data. Multimedia and individuals with smartphones and on social network sites will continue to fuel exponential growth. Yet, the impact this growing amount of data will have is unclear.

SUMMARY

A computer implemented method, computer program product, and apparatus for modeling a Big Data dataset, the method comprising creating non-specific representations of the Big Data dataset by representing, as objects in a computer model, non-specific representations including metaInformation, DataSet, BigData and Properties representations and creating non-specific representations of indices, wherein the indices are mapped to one or more key-value pairs.

DESCRIPTION OF DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

FIG. 20 is a simplified illustration of a chart denoting performance characteristics of storage mediums, in accordance with an embodiment of the present disclosure;

FIG. 23 is a simplified illustration of sequences, keys and distributions, in accordance with an embodiment of the present disclosure;

DETAILED DESCRIPTION

Figure 1:
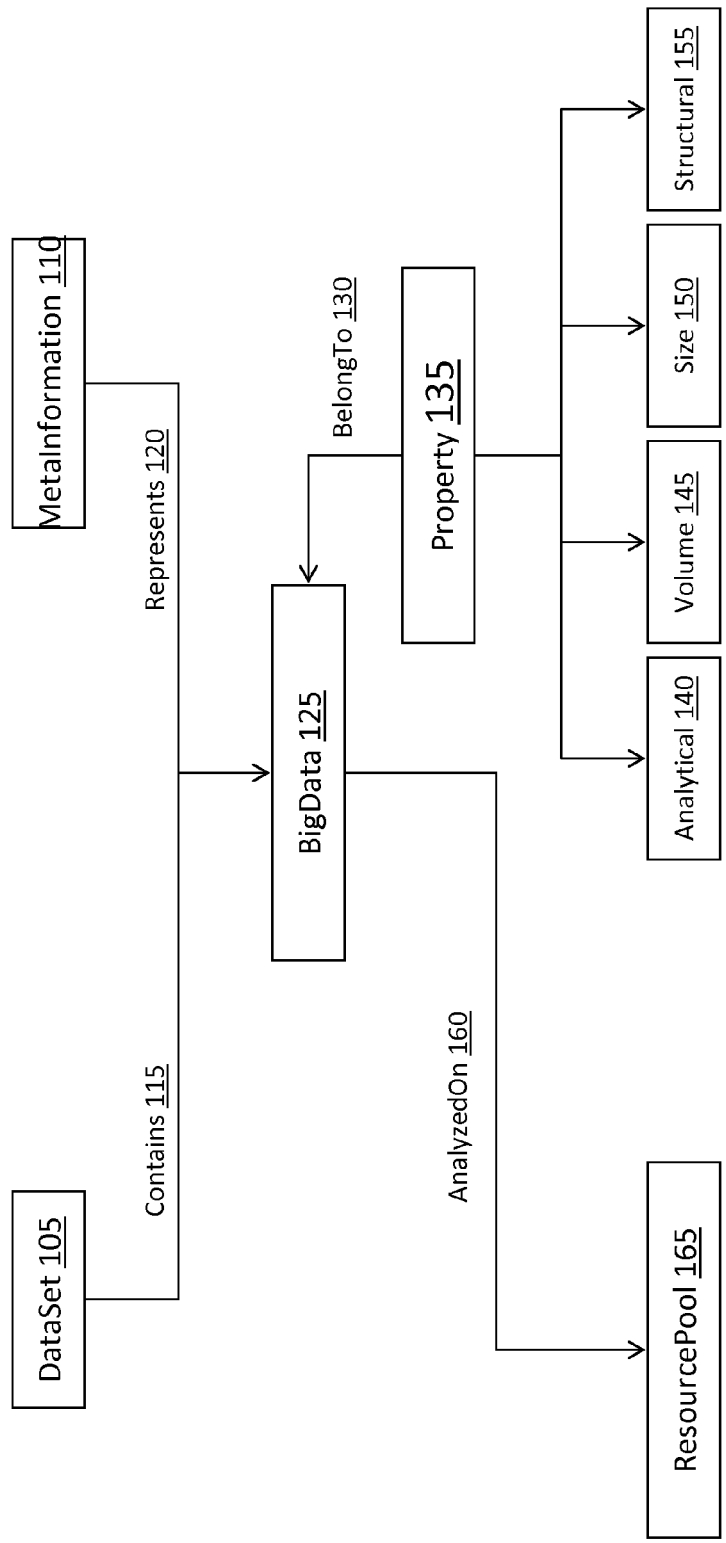
FIG. 1 is a simplified illustration of a model representation of Big Data, in accordance with an embodiment of the present disclosure.

Typically, a file system and a storage device communicate through a network or other connection. Generally, the file system or file server would request data from the storage device and there would be latency in getting the data from the storage device in the transportation medium from the storage device to the file system, delay in accessing the data on the data storage device, and delay and performing calculation on the data at the file system or server. Conventional techniques have generally focused on making more of the information readily available at the file server, or performing calculations at the storage device to enable less data to be transferred to the file system or server. However, conventional techniques have not been able to remove the need to bring information to the file server or system. Further, convention techniques often leverage disk or platter based storage, where data is stored in a sequential manner, which may require the sequence be read in order to access data in the middle of the sequence.

In an embodiment, the current disclosure enables management of small files where the content may come from few transactions or a segment of voluminous data. In certain embodiments, a file system may use modeled Big Data and optimize the information to a meta data level, so that millions of analyses may be done in efficient way. In some embodiments, a file system may keep track of modeled Big Data and provides enough information as a function to business units. In further embodiments, the meta data file system may keep track of file access, usage and purpose to help IT organizations to charge back billing. In certain embodiments, the current disclosure may enable the use of Flash storage to enable quick access to metadata. In some embodiments, Flash storage may provide a matrixed or instant type access to data without having to read through unrelated sequence of data. In further embodiments, the current disclosure may remove the need to transfer information from the data storage to the request by leveraging a metadata map with the request to provide the necessary information.

In certain embodiments, a Meta File System for transactions and voluminous data may help connect IT, business units and customers. In at least one embodiment, the current disclosure may use the meta data models for big data, specification and examples for building the meta file systems for transactions and volumes of data, subscription, functions and algorithms to define meta information for the new file system, and charge back and other utility functions that help IT to provide efficient and agile big data clouds.

Generally, the amount of data capture has grown in every area of global economy. Normally, companies are churning out increasing amounts of transactional data, capturing trillions of bytes of information about their customers, suppliers, and operations. Conventionally, millions of networked sensors embedded in the physical world in devices such as mobile phones, smart energy meters, automobiles, and industrial machines create data that is recorded and stored. Usually, as companies and organizations generate a tremendous amount of digital data that are created as a by-product of their activities. Often, enterprises may be collecting data with greater granularity and frequency, capturing every customer transaction, attaching more personal information, and also collecting more information about consumer behavior in many different environments. Usually, this activity increases the need for more storage and analytical capacity.

Typically, social media sites, smartphones, and other consumer devices including PCs and laptops have allowed billions of individuals around the world to contribute to the amount of data available. Normally, consumers communicate, browse, buy, share, and search creating large amounts of consumer data. However, conventional techniques are not able to monitor or analyze this "Big Data." Generally, conventional modeling techniques do not accommodate for or do not model the properties that define Big Data. For example, conventional techniques may not be able to perform analysis on Big Data because of the sheer number and size of transaction that would be necessary to perform the analysis. As well, conventional techniques may consider elements as attributes of the data when, to properly represent the Big Data these "attributes" may need to be considered as properties of the Big Data.

In some embodiments, "Big Data" may refer to a dataset that has a size, volume, analytical requirements, or structure demands larger than typical software tools can capture, store, manage, and analyze. In certain embodiments, "Big Data" may refer to a dataset that has a combination of attributes, such as size, volume, structure, or analytical requirements, with which typical software tools may not be able to work. In most embodiments, big data is not defined in terms of being larger than a certain number of terabytes rather, as technology advances over time, the size of datasets that qualify as big data may also increase.

In further embodiments, the definition of "Big Data" may vary by sector or industry, depending on what kinds of software tools are commonly available and what sizes of datasets are common in a particular industry. Big Data may refer to data from Digital Pathology, data from seismological surveys, data from the financial industry, and other types of data sets that are generally too large, for example in size or number of transactions, to be modeled an analyzed with conventional techniques.

Typically, organizations and business units share IT services, which may result in the creation of Big Data. Generally, the network, apps, and servers are shared and/or dedicated in many instances. Usually, of cloud and Big Data models and analytic platforms provide opportunities for the storage business. However, conventional file sizes vary depending on the verticals, domains and type of data. Conventionally solutions provide a good infrastructure to host files that are large in size, but not for smaller files.

Generally, the world has structured, semi-structured, unstructured and multi-structured information. Typically, some companies, such as Oracle, have explored the structured world, providing integrated systems address in-memory real-time analytics of structured information. Conventionally, to deal with unstructured information, these companies may use Massive Parallel Processing (MPP) and Hadoop technologies to process and transform information that is not structured into structured information and store the now structured data. However, conventional techniques that convert unstructured data to structured data lose fidelity from the data set, fidelity that may important to examining the data and this loss of fidelity may not be reconstructed or it may be expensive to reconstruct the information from the structured data.

For example, using conventional techniques it may be expensive to retrieve information that resides "inside" (random location) a file, as it needs to be read sequentially until the information is found. Using the conventional techniques, once the information is found, it may be hard to keep track of where the information is, requiring a search every time. Typically, files and unstructured information forces/imposes sequential rational, access, and analytical patterns, uncharacteristic of today's world, which may be mashed up, connected, where all the data is shared Another convention problem with Big Data may be that users are exposed to multiple file systems. Generally, each file system has a different interface and the tools to navigate files are specific to the file system and cannot be leveraged on another file system. Usually, each tool/application organizes information differently. Typically, the ways to organize information are poor and lack in contextual and semantic information. Conventionally, the high volume of big data and small data, i.e. the sheer number of files (order of thousands), makes it hard to "manage" and "organize" the files in a way that can be easily consumed. Traditional directory navigation tools may not be helpful useless, as they were designed to browse directories containing tens of files, not hundreds or thousands.

Generally, typical single hierarchical structures may not adequate to represent complex relationships (links) between files. Conventionally, content rich files may be organized in many different ways simultaneously; relationships between files typically form a mash, as opposed to a hierarchy. Traditional mechanisms focus on administrative properties of the files, and do not capture "semantics" or "contextual" information such as administrative properties: owner, date, format, size, semantic properties: key words contained in the file, other files referenced by the file, contextual properties: application and/or operation that generated the file.

In certain embodiments, the current disclosure may enable a semantically or contextual map or graph, which may provide the user with information without needing to querry the data set. In some embodiments, the current disclosure may enable a Viewer and Role, <Viewer, Role> for a Big Data set, where not all data in the Big Data may be relevant to each Viewer. In some embodiments, a small percentage of the Big Data may be relevant for a single <viewer, role> pair. In other embodiments, not all the data that is relevant to one <viewer, role> may be relevant to other pairs. In at least some embodiments, each group or cluster of <viewer, role> pairs may be interested in a different subset of the data or interested in different aspects of the data.

In certain embodiments, the current disclosure may decouple content from a file system (FS) structure and enable one file to be shared and viewed by multiple file systems and multiple users. In at least one embodiment, the current disclosure may enable information to be abstracted or harvested from the content of the file that may not otherwise by captured by the underlying FS. In other embodiments, knowledge may be inferred or learned from the information harvested and form the content of the file, where previously such knowledge may not have been obtained automatically or preserved.

Generally, Big Data is Multi Structured and may be conventionally stored, analyzed and managed each type of information in a number of different ways. In some embodiments, structured data may be stored in Block based, SQL, and RDMS type databases. In other embodiments, semi-structured data may be stored in XML Data Files, in File Based systems, and in Hadoop Map Reduce. In further embodiments, quasi-structured data may be data containing some inconsistencies in data values and formats, e.g., Web clickstream data. In some embodiments, unstructured data may be text documents that could be subject to analytics over text or numbers such as file based data, Hadoop MapReduce, and HDFS data. In other embodiments, unstructured data may be images and video such as file based data, and data streamlined with technologies such as MapReduce, or Scale Out NAS data. Typically, it may be difficult to process information stored in all different formats, cross-analyze content, or visualize and gain insight into the important information spread all over the different formats;

Generally, storing data using conventional techniques results in a loss of Intermediate Results. Conventionally, MapReduce technologies offer a way to distribute processing of information (map) and then combine it into a result (reduce). However, these conventionally technologies usually compute such that the data in the intermediate steps is often discarded. Thus, in these conventionally techniques, when the information is required again, it is often computed again. In some embodiments of the current disclosure, the same intermediate information (map) may be "reduced" in many different ways when the intermediate information may offer insight that maybe extremely valuable as an abstract, pre-processed way of looking into the information;

Conventionally, there is not a way to provide cross-correlation across different perspectives. Generally, it may be difficult to process information stored in all different formats, cross-analyze content, or visualize and gain insight into the important information spread all over the different formats. As used herein, the following may be useful in understanding the following term:

Data may be any collection of bits. An Information System may be a system that provides and support a structure to create, update, delete, store, organize and manage data. Examples of Information Systems may be File Systems, Object Stores, Database Systems, and a Block. A Marker, also referred to here as meta-information, may be a piece of data/information which can be associated (connected) to data. A Marker Cluster may be a set of markers. A Mark may be a property of a Data. A Maker may consist of a set of Marks. A set of Marks may define a Marker A user may be a <Person, Role>, where a user is a pair identifying a person and one of his roles. A person may have/assume different roles. Security and access privileges to Markers may be granted to users, and maybe derived and verified in the context of the privileges assigned to People and their Roles. Users may be connected to Markers and Marker Clusters Modeling Big Data Referring to FIG. 1, this figure illustrates an exemplary abstract model for Big Data in accordance with the current disclosure. The classes, objects, and representations shown in the model may be an extension of known distributed system models, such as the EMC/Smarts Common Information Model (ICIM), or similarly defined or pre-existing CIM-based model and adapted for the environmental distributed system, as will be discussed. EMC and SMARTS are trademarks of EMC Corporation, Inc., having a principle place of business in Hopkinton, Ma, USA. This exemplary model is an extension of the DMTF/SMI model. Model based system representation is discussed in commonly-owned U.S. patent application Ser. No. 11/263,689, filed Nov. 1, 2005, and Ser. No. 11/034,192, filed Jan. 12, 2005 and U.S. Pat. Nos. 5,528, 516; 5,661,668; 6,249,755 and 6,868,367, and 7,003,433, the contents of all of which are hereby incorporated by reference. An example of a Big Data Set may be found in commonly-owned U.S. patent application Ser. No. 12/977,680, filed Dec. 23, 2010, entitled "INFORMATION AWARE DIFFERENTIAL STRIPING" the contents of which are hereby incorporated by reference. An example of modeling Big Data Set may be found in commonly-owned U.S. patent application Ser. No. 12/977,680, filed Sep. 30, 2011, entitled "MODELING BIG DATA" the contents of which are hereby incorporated by reference. An example of analyzing Big Data Set may be found in commonly-owned U.S. patent application Ser. No. 12/977,680, filed Sep. 30, 2011, entitled "ANALYZING BIG DATA" the contents of which are hereby incorporated by reference.

Generally, referred-to US Patents and patent applications disclose modeling of distributed systems by defining a plurality of network configuration non-specific representations of types of components (elements or devices) managed in a network and a plurality of network configuration non-specific representations of relations among the types of managed components and problems and symptoms associated with the components and the relationships. The configuration non-specific representations of components and relationships may be correlated with a specific Big Data set for which the associated managed component problems may propagate through the analyzed system and the symptoms associated with the data set may be detected an analyzed. An analysis of the symptoms detected may be performed to determine the root cause—i.e., the source of the problem—of the observed symptoms. Other analysis, such as impact, fault detection, fault monitoring, performance, congestion, connectivity, interface failure, in addition to root-cause analysis, may similarly be performed based on the model principles described herein.

Refer again to the example embodiment of FIG. 1. FIG. 1 illustrates an example embodiment of a data hierarchy for a model that may be used to model Big Data. In this embodiment, a data set may have one or more properties that are bigger in size or volume or analytical properties that may normally be modeled. In FIG. 1, DataSet 105 Contains 115 Big Data 125 and MetaInformation 110 Represents 120 Big Data 125. Meta Information 110 may be classes or objects that hold key attributes of Big Data 125 which may be used for a quick analysis.

Big Data 125 may also have Properties 135 which Belong To 130 Big Data 135. Properties 135 may contain properties that are Analytical 140, Volume 145, Size 150, and Structural 155. In some embodiments, there may be an analytical property, which may be a class or object that contain Transactional Properties or Quantitative/Numerical Properties or Iterative or HPC properties to the purpose of analytics and reporting. In certain embodiments, there may be a volume property class or object which may contain the information of List or Hierarchical or Sequential or Mash or Blogs. Big Data 125 may be Analyzed On 160 Resource Pool 165. Resource Pool 165 may represent the available computing, storage and network resources, physical and virtual, for the purpose of analysis, storage, and transfer of the analyzed information.

Figure 2:
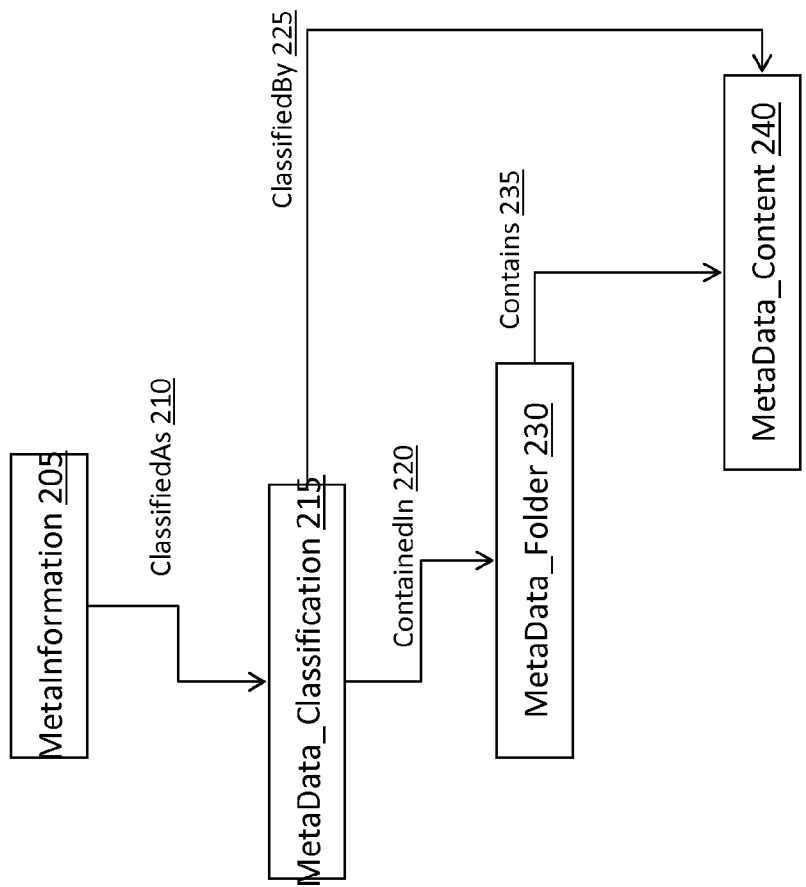
FIG. 2 is a simplified illustration of a model representation of MetaData classification for Big Data, in accordance with an embodiment of the present disclosure.

Refer now to the example embodiment of FIG. 2. FIG. 2 illustrates some objects and representations that may be useful in modeling big data. Meta Information 205 may be Classified As 210 Meta Data Classification 215 which may be Contained In 220 Metadata Folder 230, which Contains 235 metadata content 240. Metadata classification 215 may be Classified by 225 Metadata Content 240.

In some embodiments, Meta Information may have a set of key attributes. In some embodiments, the set may include some or all of the attributes of sources, creation time, file format, blocks, object store, DataBase-Type, Linked-Meta-data-List, growth rate, last used, analysis-Type-List, analysis-Policy-List, compute-Resource-Used.

Figure 3:
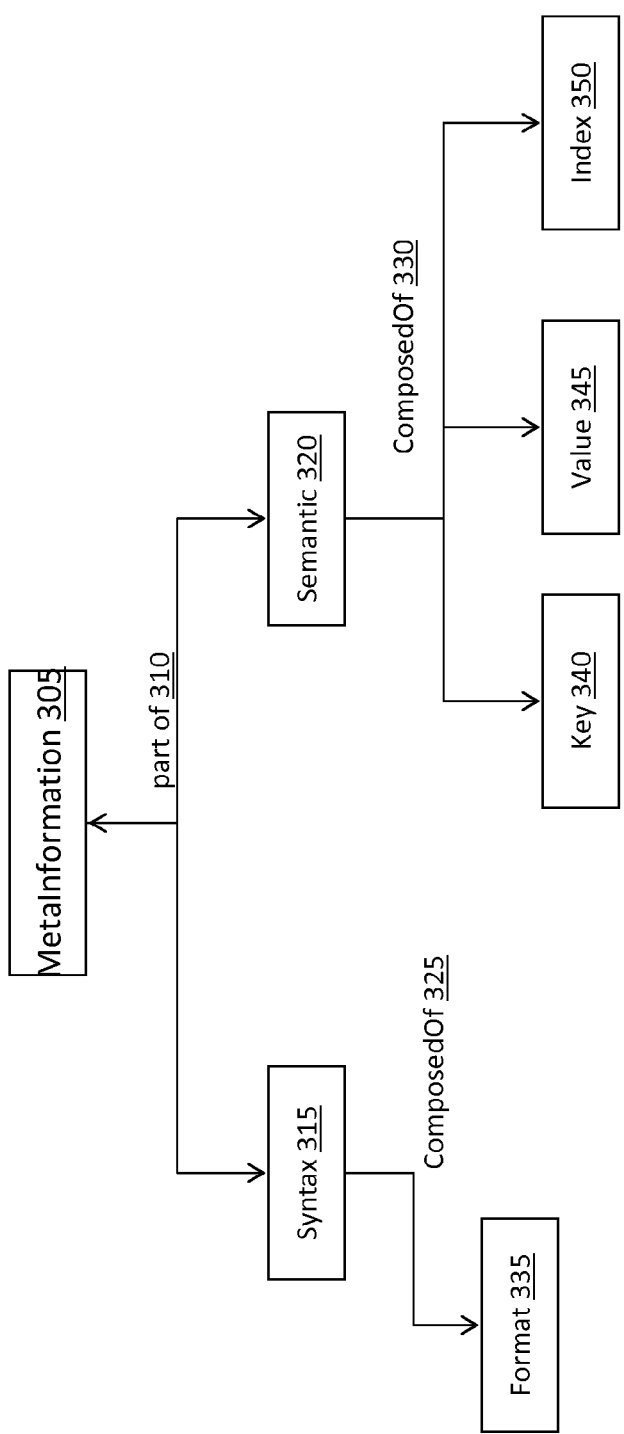
FIG. 3 is a further simplified illustration of a model representation of metadata information for Big Data, in accordance with an embodiment of the present disclosure.

Refer now to the example embodiment of FIG. 3. FIG. 3 illustrates some objects and representations that may be useful in modeling big data. In FIG. 3, MetaInformation 305 may be Part Of 310 Syntax 315 and Semantic 320 and may be a class or object that holds the key information about the big data. Syntax 315 may be a class or object that represents the syntactic meta information of the big data. In FIG. 3, Syntax 315 may be Composed Of 325 Format 335. In the example embodiment of FIG. 3, Format 335 may be a class or object which represents the format in which data is formatted. In the embodiment of FIG. 3, Format 335 may also specify an algorithm or general pattern. Semantics 320 may be a class that represents the semantics of the big data. Semantic 320 may be Composed Of 330 Key/Value Pair 340, 345, which may be a class or object which helps to decipher the meaning of the big data based on key/value of certain information. Semantic 320 may also be Composed Of 330 Index 350. Index 350 may be a class or object that points to a specific meaning for the purposes of semantic look ups.

Meta Data Information

Figure 4:
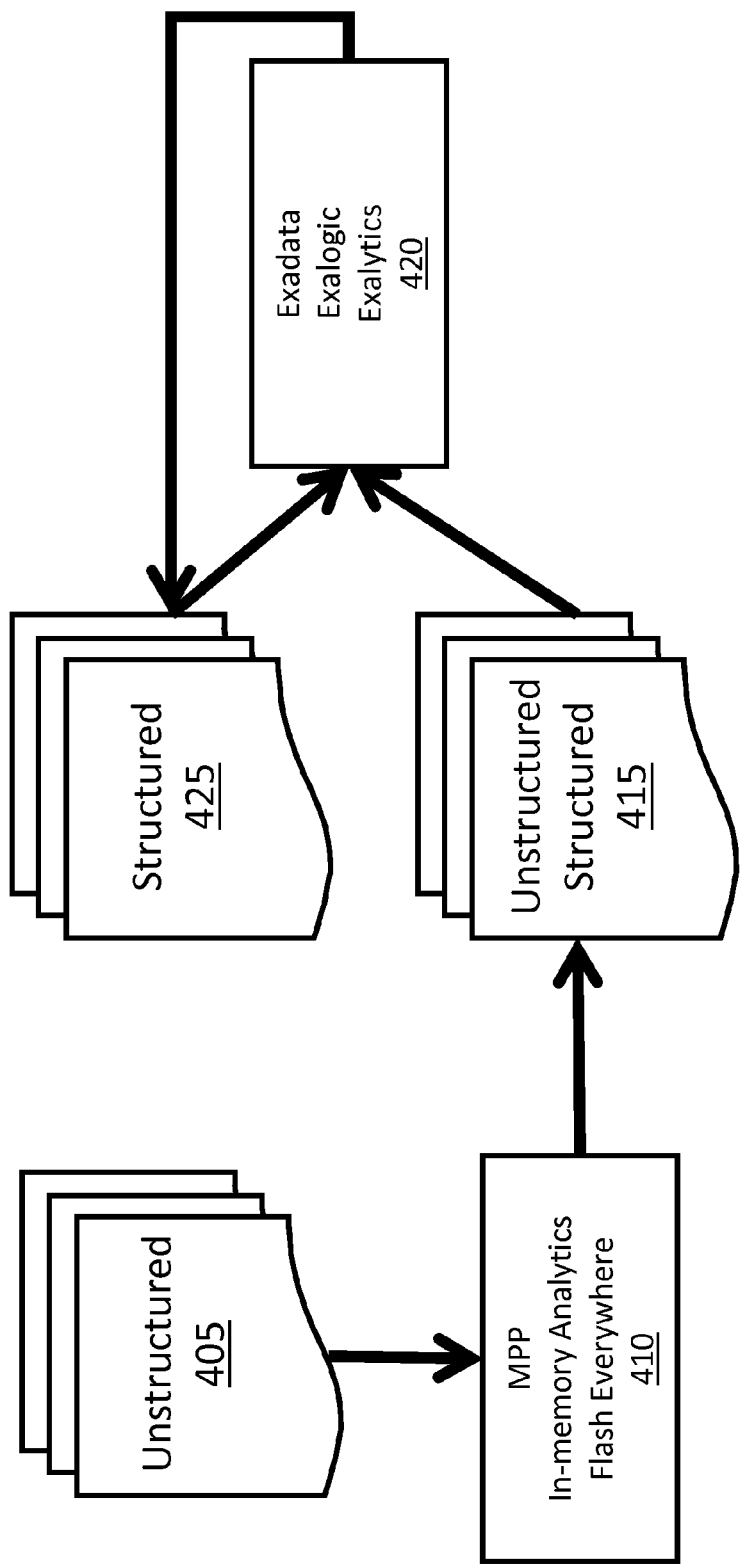
FIG. 4 is a simplified illustration of a model representation of transforming unstructured data to structured data, in accordance with an embodiment of the present disclosure.

Typically, conventional techniques have used Massive Parallel Processing (MPP) and Hadoop type technologies to process and transform information and Big Data that is not structured into structured information. Generally, however, this requires the unstructured data to be forced into a tabular (table oriented) representation of the data. For example refer to FIG. 4. Generally, unstructured data 405 would be categorized via a tool, such as MPP 410 to unstructured and structured data 415. This data would have analytics performed on it by an analytics tool 420 and be transformed to structured data 425, losing some of the fidelity of the data.

In certain embodiments, the current disclosure enables modeling and analysis of structured, semi-structured, unstructured and multi-structured information. In some embodiments, an abstraction layer lay may be created which may consist of a graph of "marks" that point to pieces of information in the world, structured or otherwise. In certain embodiments, these "marks" represent topics or information of interest that may be contained in the world and may point to where those points of interest can be found in the world. In further embodiments, these marks may group related pieces of "data" in the Big Data world providing Semantics information on the content of this information.

Figure 5:
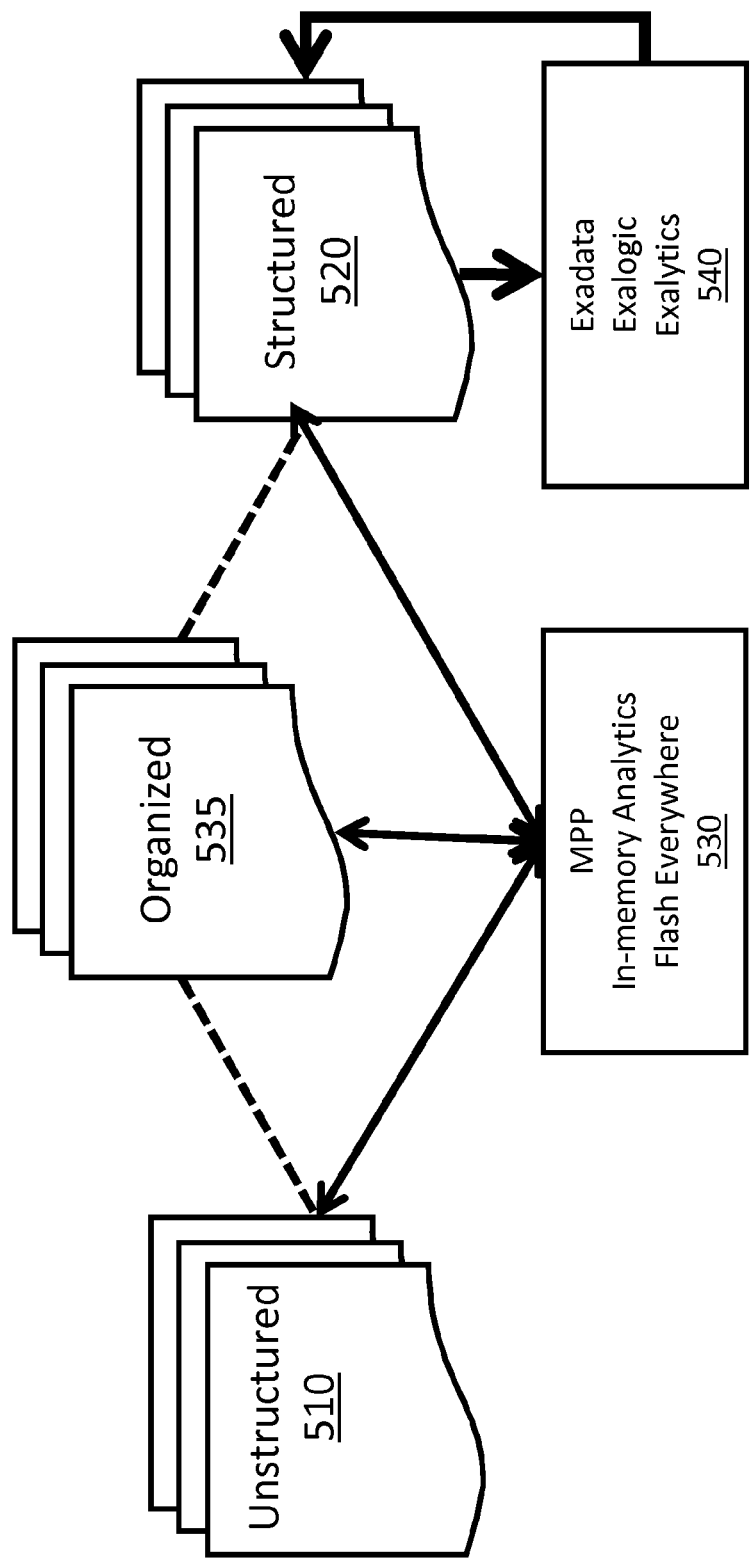
FIG. 5 is a simplified illustration of a model representation of enabling a representation of both unstructured and structured data, in accordance with an embodiment of the present disclosure.

For example, refer to the example embodiment of FIG. 5. Unstructured data 510 and structured data 520 may be used and mapped by MPP 530 into organized data 535, which may provide a mapping and means of access to both the structured and unstructured data. In some embodiments, the organization may provide not only accessed to the structured data that may be lost if storing it as structured data, but also may provide further mappings or analytical information about the data.

In at least some embodiments, analytics may not be performed on the entire content of the Big Data World, instead, each "project" or set of analysis may have a "Context." In some embodiments, the contest may consist of a set of "key words" or "topics" which may be referred to as "marks." In most embodiments, each project or set of analytics to be performed on the project such "finding", "accessing", "analyzing", etc (e.g., counting, understanding, comparing), may be represented the presence or not of these marks.

In some embodiments, within a context, these marks may searched for and analyzed multiple times and information for these marks, their presence and location should not be deleted, and instead may be maintained in a fast memory to enable this information to be readily available. In some embodiments, this abstraction layer may not be independent of the underlying Information System (e.g., File system, object store, database, etc.) rather it may provide a map to this information. In certain embodiments, the layer of abstraction may be a way of organizing information that may be scattered across multiple file systems.

In further embodiments, once the marks are created much of the analytics of the data set may be performed on the marks without accessing the underlying data set. In certain embodiments, if the underlying dataset changes, the marks indexes may need to be updated. In most embodiments, different marks may be created for different analytics and the marks may be specific to the information needed to be examined by a user of the dataset.

In some embodiments, a project may define additional marks to be identified and searched for in the data. In certain embodiments, a project may find information in the data that goes beyond the information captured on a mark. In a particular embodiment, marks may represent intermediate results on computations and point to information where the intermediate result was obtained. In another embodiment, for example when analyzing a Genome and counting the presence of a "repeatable" string, a mark may be a pair <"string", "number of occurrences"> and may point to files and the location where that "string" had been found a certain "number of occurrences." In this embodiment, when a processing activity is executed to count that string, the activity may find each occurrence and may have to traverse the entire string. In this embodiment, the process may find and counts and "knows" where each "string" is.

Figure 6:
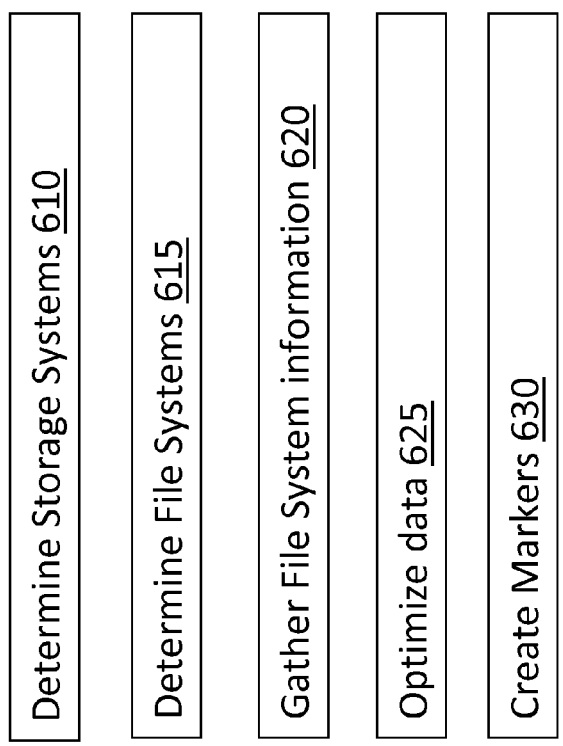
FIG. 6 is a simplified method for creating metadata markers, in accordance with an embodiment of the present disclosure.
Figure 7:
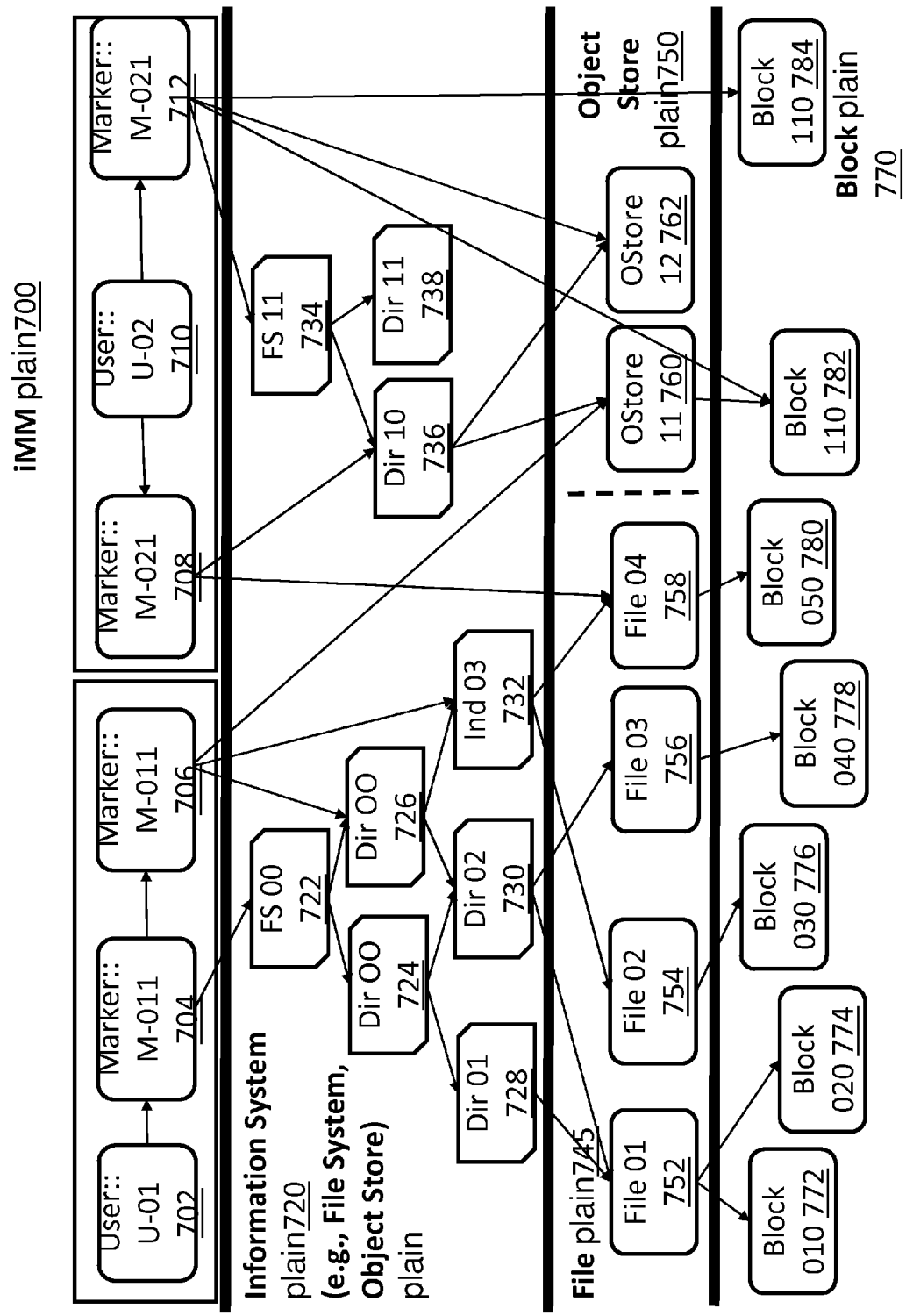
FIG. 7 is a simplified illustration of a model representation of metadata mapped across an informational plane, a file plane, an object store plane, and a block plane, in accordance with an embodiment of the present disclosure.

For example refer to the example embodiment of FIGS. 6 and 7. In intelligent marker miner (iMM) Plane 700, there are two user marker pairs in which user 702 is connected to marker 704 and marker 706. As well, User 710 is connected to marker 708 and marker 712. These user marker pairs represent views for each user into the underlying data through the use of a metadata map. In this embodiment, Marker 708 is linked to file 758 in File plane 720, which is linked to Block 780 in the Block Plane. Marker 708 is also linked to Directory 736, which is linked to Object store (OStore) 760 and OStore 762 in the object store plane, where OStore 760 is linked to block 782 in the Block Plane.

The example embodiment of FIG. 7 may be created by determining the storage systems in the block plane 770 on which the data resides (step 610). The file systems in the information plane may be determined (step 615). The file system information in the file plane 745 may be gathered (step 620). The gathered data may be optimized (Step 625). Markers 704, 706, 708, 710, and 712 may be created based on the data (step 630). FIGS. 6 and 7 represent example embodiments of how a metadata graph may be created to represent how data for a particular user may be mapped to a subset of the data.

Figure 8:
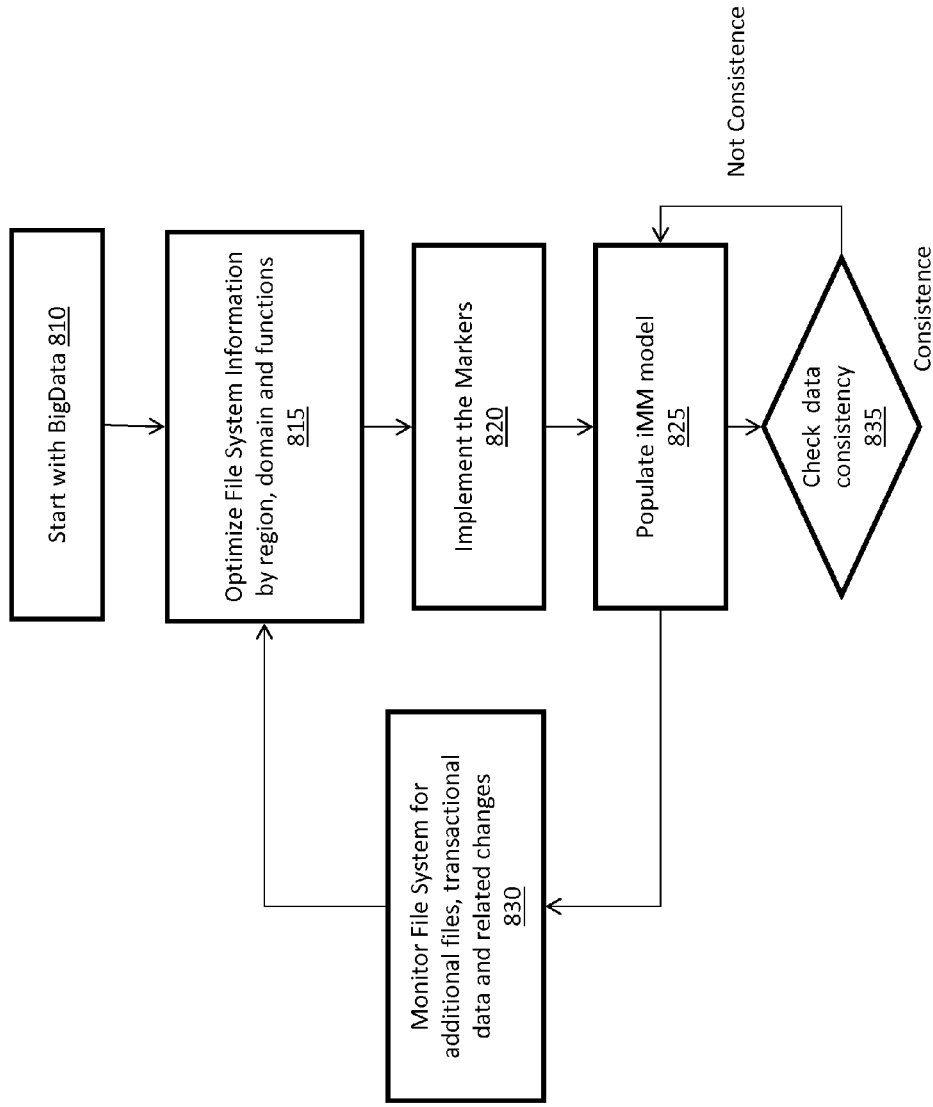
FIG. 8 is a simplified method for creating and populating an IMM model, in accordance with an embodiment of the present disclosure.
Figure 9:
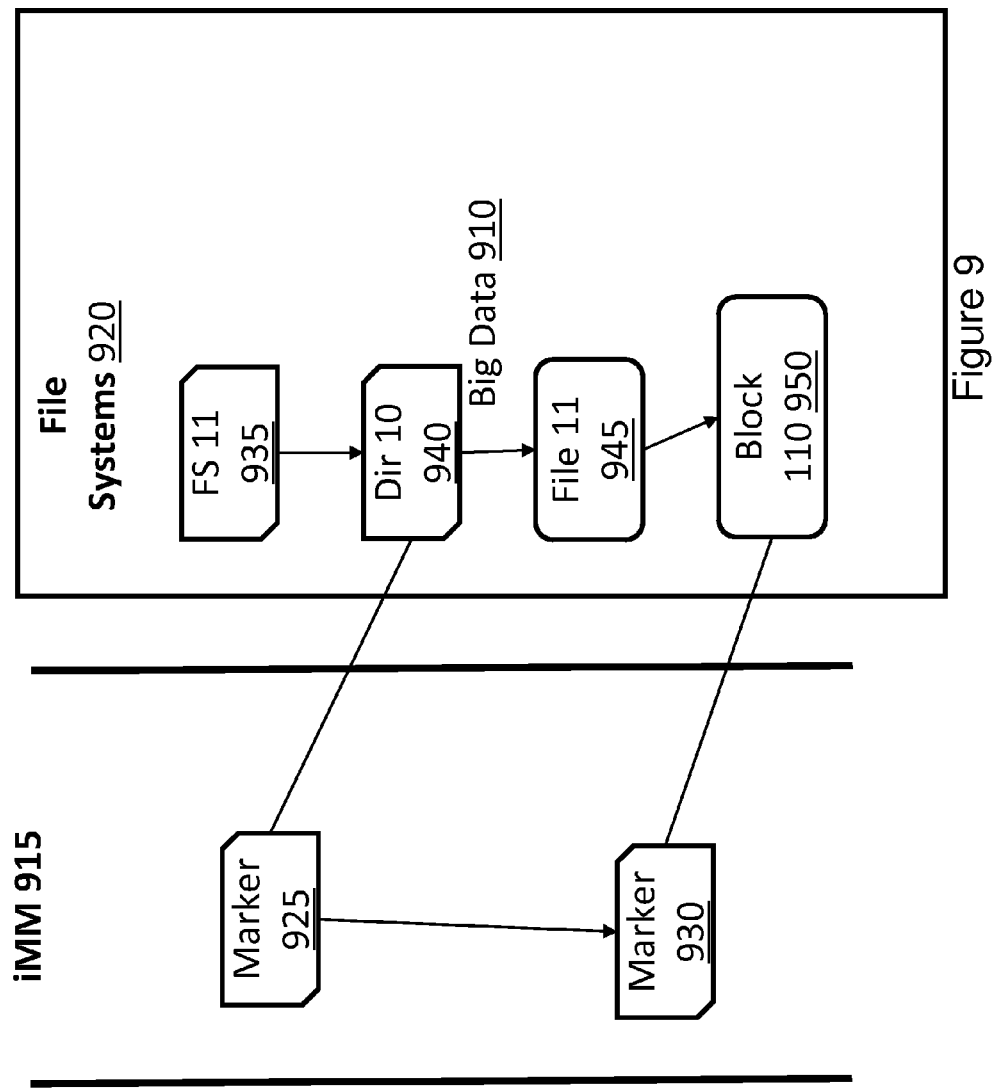
FIG. 9 is a simplified illustration of a model representation of metadata in an IMM plane mapped to file systems, an object store plane, and a block plane, in accordance with an embodiment of the present disclosure.

Refer now to the example embodiments of FIGS. 8 and 9. The Big Data 910 may be chosen (step 810). The file system information 920 may be optimized by region, domain, and other functions (step 815). The markers 925, 930 may be implemented (step 820). The iMM model 915 may be populated with data from the File systems 920 (step 825). The model may be checked for consistency (step 835). The model may be monitored (step 830).

In certain embodiments, an abstract representation/model of an Information System may be created using markers and connections between the markers, markers and data. In some embodiments, the markers may capture properties of data, including, but not limited to administrative properties, contextual properties, and semantic properties of the data. This modeled representation may be used as a means to organize and manage data, including, but not limited to the whole structure of the file system (directories and sub-directories), the abstraction of files, and the content stored within the file.

In further embodiments, DRAM and Flash may be leveraged to maintain a metadata representation in memory for fast access. In other embodiments, maintaining the representation/model may enable greater scalability as less information is stored, faster access as information is already organized, dynamic model representation changes, and in real time, enabling multiple marker-models to co-exist simultaneously, and enabling organizational marker-models that are meshed (cyclical) not just hierarchical. In some embodiments, marker models may be dynamically extended/changed to capture more abstractions of interest. In most embodiments, the representation may be file system "agnostic" and may hide the details of the underlying file system.

In further embodiments, the representation may serve as an integration to multiple file systems. In some embodiments, the representation may be a file system of file systems. In certain embodiments, one of the file systems may be in the cloud.

In certain embodiments, administrative tasks may be performed by the native file systems. In other embodiments, the representation may not allow writing of the actual files. In some embodiments, the representation may not remove the files. In other embodiments, abstract representations may be updated dynamically and in real time.

In certain embodiments, analysis may be performed on the abstract model or metadata. In certain embodiments, semantic and contextual information through may be inferred through relationship/link traversal. In other embodiments, capacity planning may be performed. In further embodiments, usage of space based on content creation rate per application/user/time of the day may be estimated. In other embodiments, statistics on properties of the files may be calculated.

In further embodiments, an abstract model may be used to represent and enforce Security constraints on operations to the files. In some embodiments, the model may be used to control access to content, access to abstract representations, control the ability to create, update, an perform analysis on the abstract representation. In some embodiments, the abstract model may keep pointers to specific locations in the file where "relevant" content can be found, e.g <Keyword>, <Block-Address, Byte-Number>. In at least some embodiments, connections may be created either manually or automatically, while others may be "inferred" manually or automatically, based on other existing connections.

In other embodiment, an abstract model representation may used to link multiple different Big Data models. In most embodiments, connections between systems may not be multi-exclusive. In certain embodiments, there may be as many connections as necessary and the connections coming out of relations may not need to be to the same "type" of entity. In further embodiments, the same entity in the abstract model may connect to a file system, a sub-directory and a block all at the same time. In alternative embodiments, the abstract model may be tied to one or more of the following: File System, Virtual File System, Object Store, Virtual Object Store, Directory or sub-directory, File, Block, Virtual Block.

In certain embodiments, an implementation of an abstract models may be persisted in permanent storage so that the model need not be calculated each time it is to be analyzed. In other embodiments, as the model changes, the previous model may be stored to analyze changes to the model over time. In some embodiments, aspect of the model may be analyzed by outside tools such as EMC's GreenPlum. In further embodiments, multiple user views may be created, where different users may access different perspectives/views of the abstract model based on interest and areas of focus. In certain embodiments, different views may be accessed based on Viewers interest and security permissions. In further embodiments, depending on the user/view combination a subset of the abstract model may need to be up loaded into main memory. In still further embodiments, multiple views may be maintained simultaneously for the same or multiple users.

In a particular embodiment, an abstract model representation may be used as "meta information" for the underlying File System to enable "management" or "organization" of the underlying files in a more optimized manner. In this embodiment, files/blocks with multiple connections to the abstract model may be spread across the storage arrays and may reside in the lower storage tiers, and a higher connection index may indicate a higher probability of access.

In some embodiments, short-cuts may be created to represent the dependencies between keys (a type of a Mark) and the data to which they are related. In other embodiments, persistent storage for Key-Value pairs/map function may be provided locally in nodes and globally for additional processing/visualization. In some embodiments, simultaneous view and analytics of the same data may be available from different perspectives. In further embodiments, the abstract model may be used as a visualization tool to graphically present the data and relations between the data.

Figure 10:
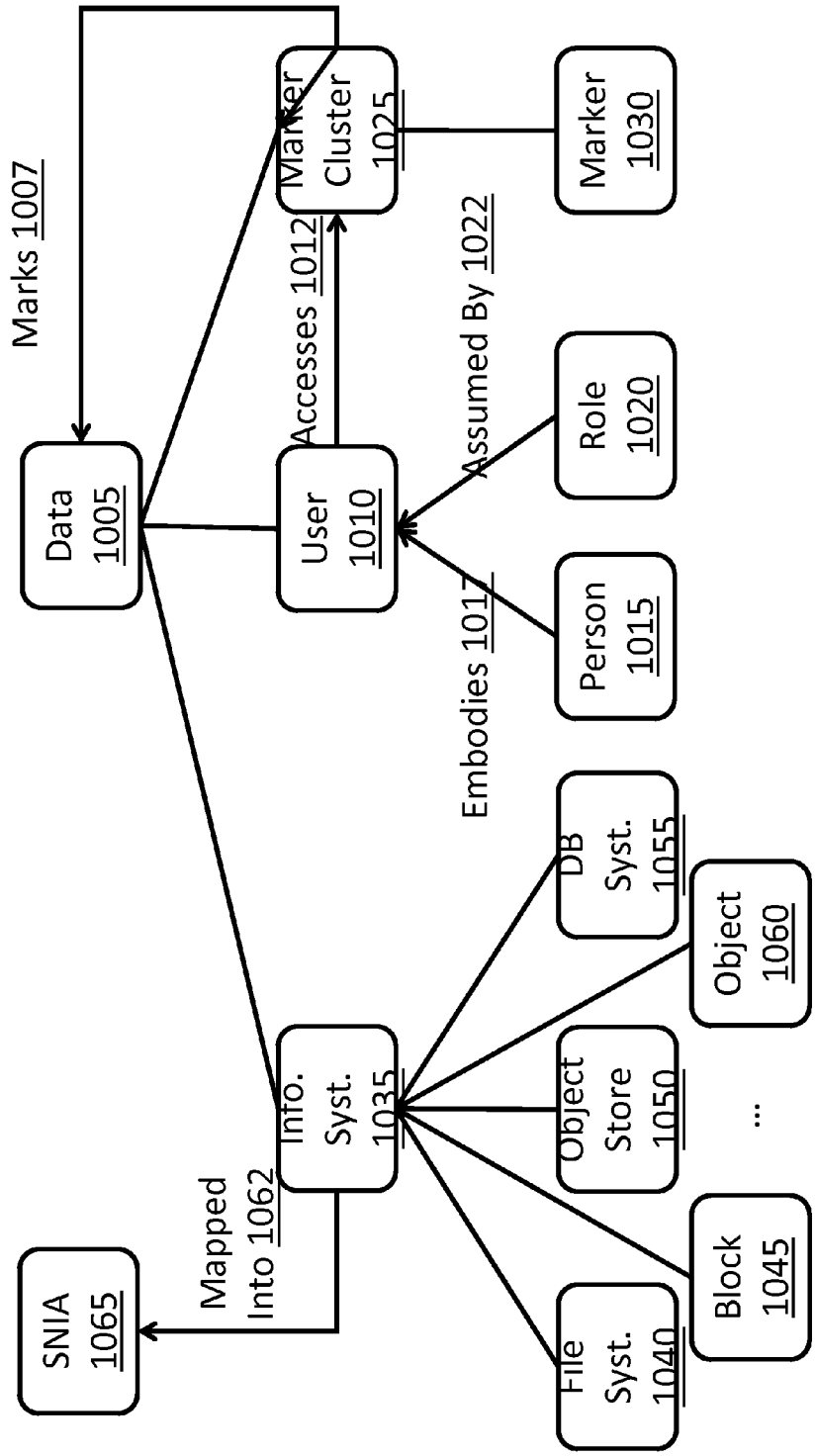
FIG. 10 is a simplified illustration of a model representation of a data model for metadata, in accordance with an embodiment of the present disclosure.

Refer now to the example embodiment of FIG. 10. FIG. 10 represents a sample model that may be used to model the maker information. Data 1005 contains information systems 1035, File systems 1040, Blocks, 1045, Object Store 1050, Database System 1055, and Object 1060 and is mapped into 1062 SNIA 1065. The data is marked 1007 by Marked Cluster 1025 which is make up of markers such as marker 1030. Markers may be accessed 1012 by users, such as user 1010, where each user may embody 1017 a person 1015 and a assume 1022 a role 1020.

Figure 11:
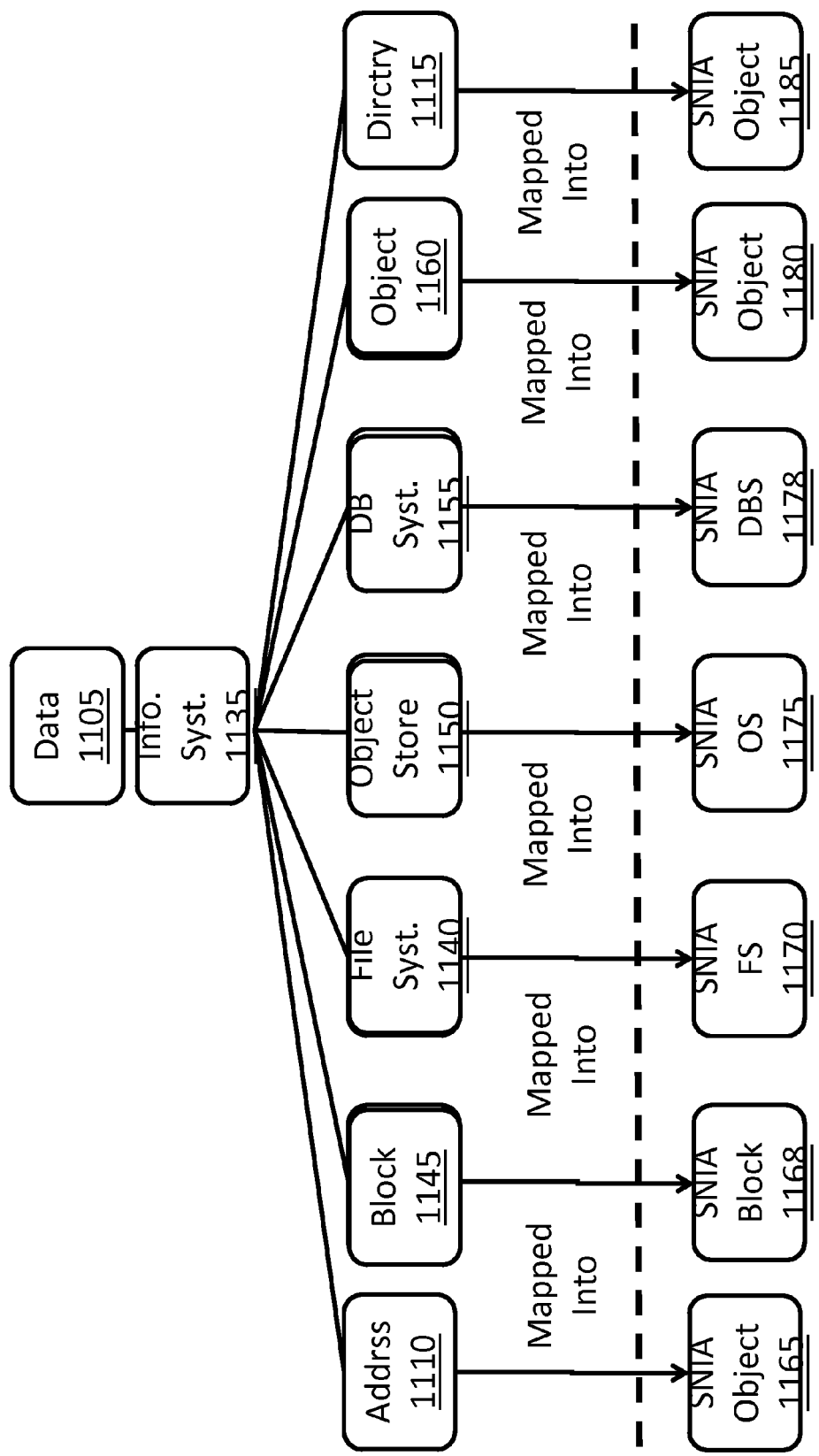
FIG. 11 is a simplified illustration of a model representation of a Connecting to storage network industry association (SNIA) via refined relationships, in accordance with an embodiment of the present disclosure.

Refer now to the example embodiment of FIG. 11. Data 1105 is mapped from information systems 1135. The data in information systems 1135 is mapped to addresses 1110, blocks 1145, File systems, 1140, object store 1010, database systems 1155, objection 1160, and Directory 1115. Directory 1115 is mapped to SNIA object 1185. Objection 1160 is mapped to SNIA object 1180. Database system 1155 is mapped to SNIA DBS 1178. Object Store 1150 is mapped to SNIA OS 1175. File system 1140 is mapped into SNIA FS 1170. Block 1145 is mapped into SNIA Block 1168. Address 1110 is mapped into SNIA Object 1165.

Figure 12:
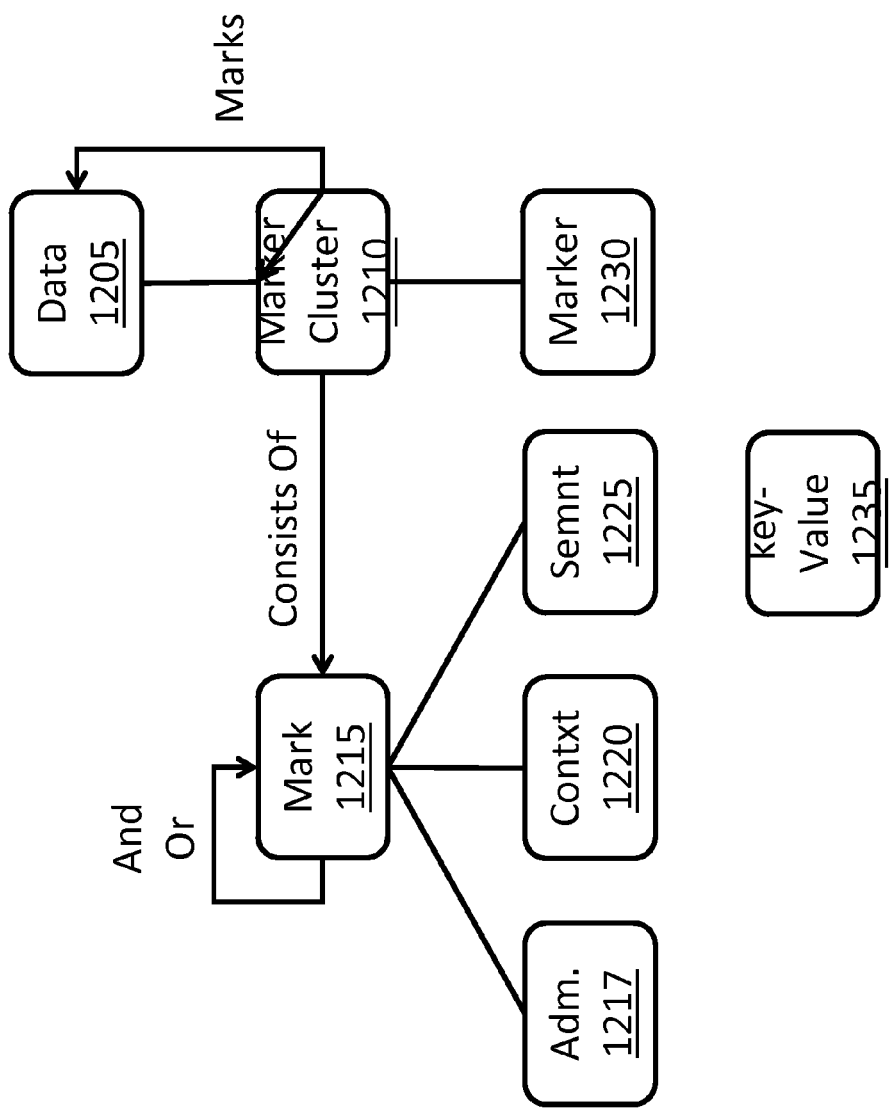
FIG. 12 is a simplified illustration of a model representation of a metadata markers and properties, in accordance with an embodiment of the present disclosure.

Refer now to FIG. 12, which represents an example embodiment of dividing the data into markers. Marker cluster 1210, consisting of marks 1215, marks data 1205. The marker cluster has a set of markers 1230. The marks may be administration marks 1217, contextual markers, 1220, or semantical markers.

Figure 13:
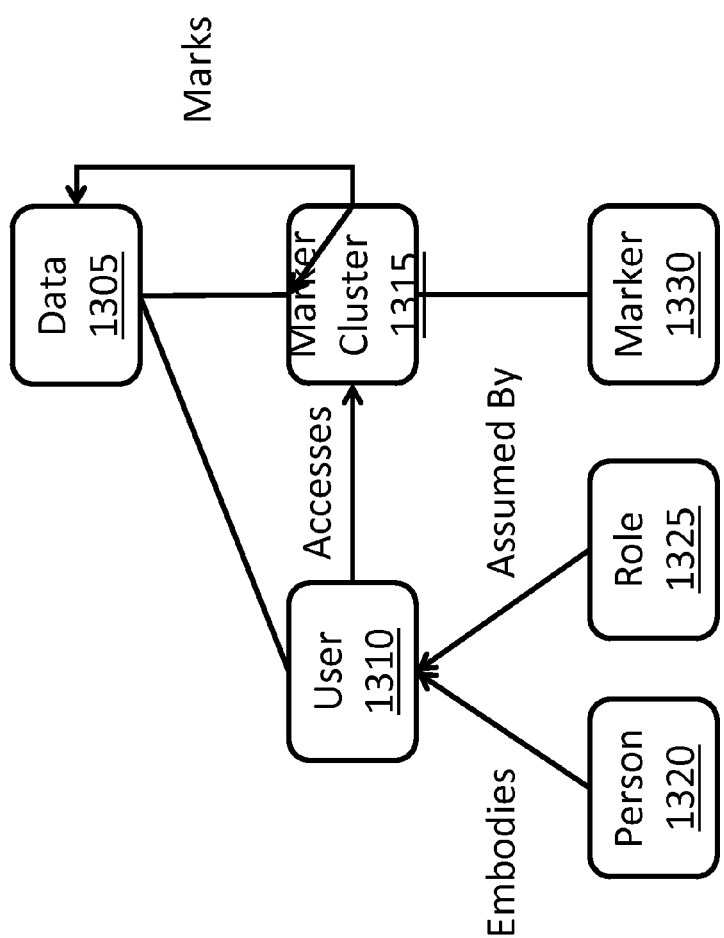
FIG. 13 is a simplified illustration of a model representation of a sample user maker cluster pairs in respect to the data model, in accordance with an embodiment of the present disclosure.

Refer now to the example embodiment of FIG. 13. User 1310 is embodied by person 1320 and assumes role 1325. User 1310 accesses marker cluster 1315 which is made up of marker 1330 and marks data 1305.

Figure 14:
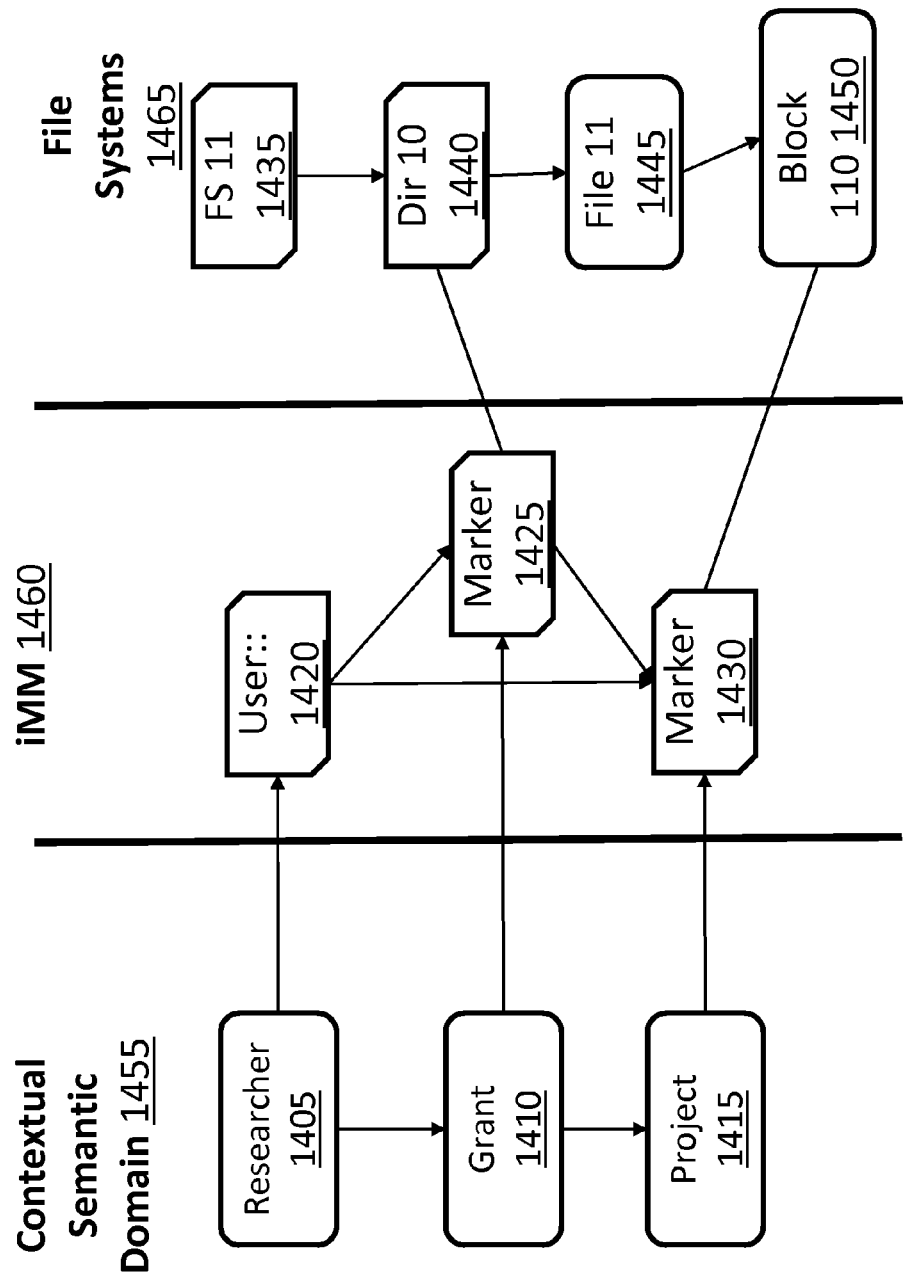
FIG. 14 is a simplified illustration of a model representation of connecting domains via an iMM model mapping, in accordance with an embodiment of the present disclosure.

Refer now to the example embodiment of FIG. 14. File systems 1465 has file system 1435 and directory 1440, file 1445 and block 1450. Markers 1425 and 1430 are mapped to directory 1440 and block 1450 respectively. User 1420 is mapped to marker 1425 and marker 1430. User 1420, Marker 1425 and Marker 1430 are in the IMM domain 1460. The IMM domain 1460 is mapped to a contextual semantic domain 1455. Domain 1455 has researcher 1405 which is mapped to user 1420. Researcher 1405 is also mapped to grant 1410, which is in turn mapped to marker 1425. Grant 1410 is mapped to project 1415, which is mapped to marker 1430.

Figure 15:
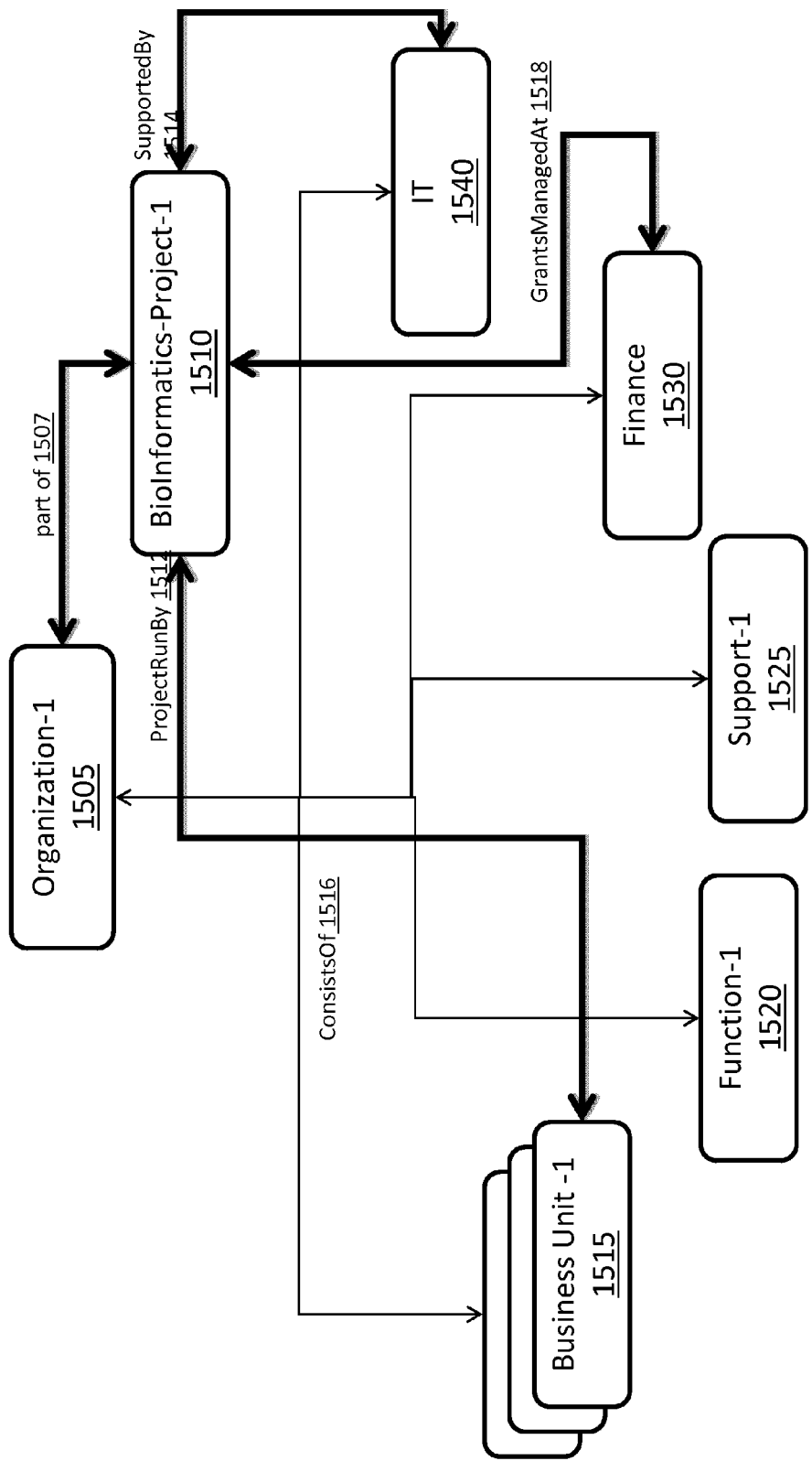
FIG. 15 is a simplified illustration of a model representation of a semantic domain view in a bioinformatics project, in accordance with an embodiment of the present disclosure.
Figure 16:
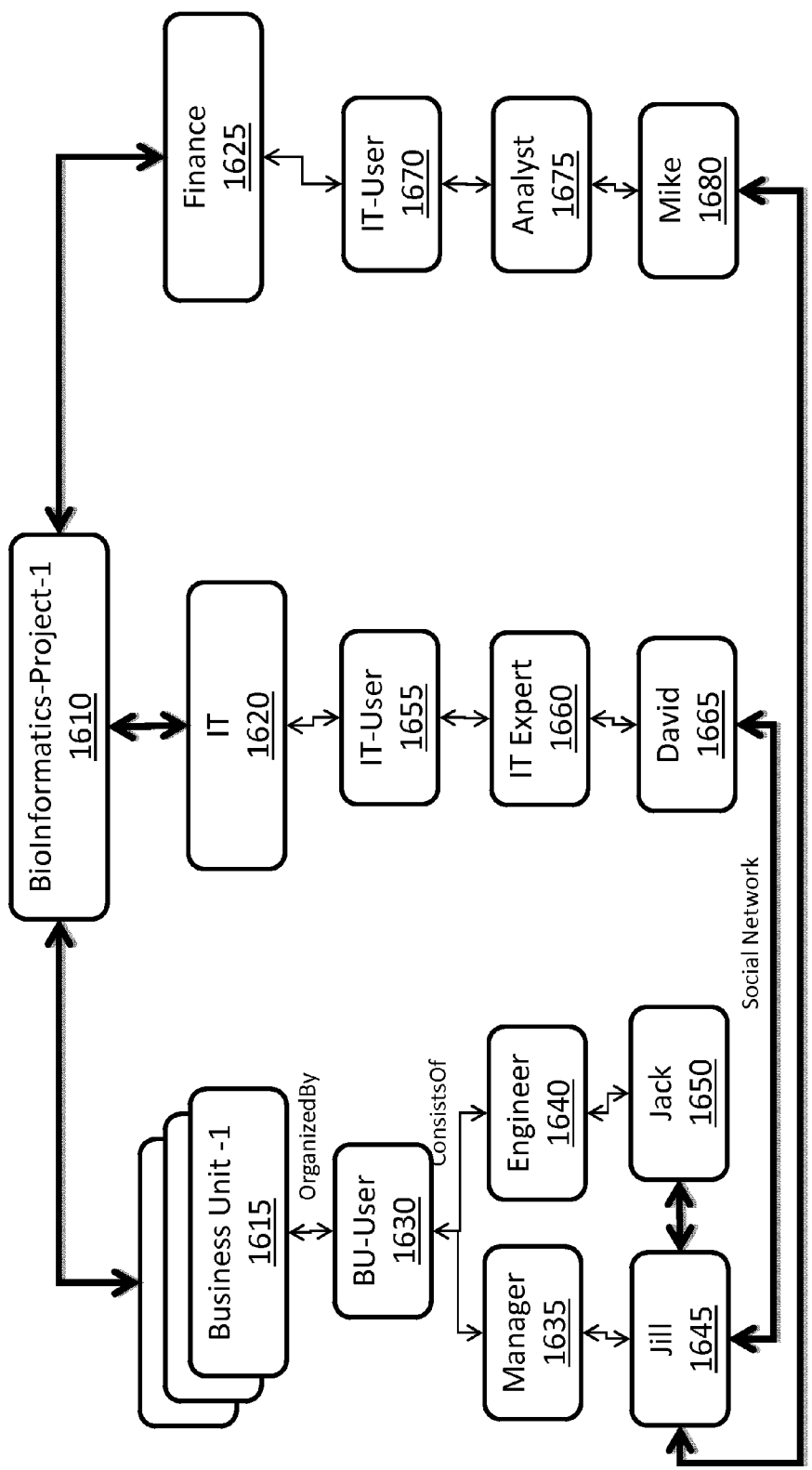
FIG. 16 is a simplified illustration of a model representation of a user view in a bioinformatics project, in accordance with an embodiment of the present disclosure.

Refer now to the example embodiment of FIG. 15. In FIG. 15 Bioinformatics project 1510 is run by business unit 1515 and is supported by IT 1540. Bioinformatics project 1510 is part of organization 1 and has grants managed at finance 1520. Organization 1 has function 1520 and is supported by support 1525. Organization 1 is also connected to finance 1530. Business unit 1515 is also connected to IT 1540.

Refer now to the example embodiment of FIG. 15. Bioinformatics project 1610 is related to Business Unit 1, IT 1620 and Finance 1625. Business unit 1615 is optimized by Business User 1630, which consists of Manager 1635 and Engineer 1640. Manager 1635 is Jill 1645. Engineer 1640 is Jack 1650. Jack 1650 is connected to Jill 1645 over a social network. IT 1620 has IT user 1655 which is connected to IT expert 1660, which is David 1665 who is connected via a social network to Jill 1645. Finance 1625 is made up of It user 1670, who is analyst 1675, who is mike 1680. Mike 1680 is connected to Jill 1645.

Figure 17:
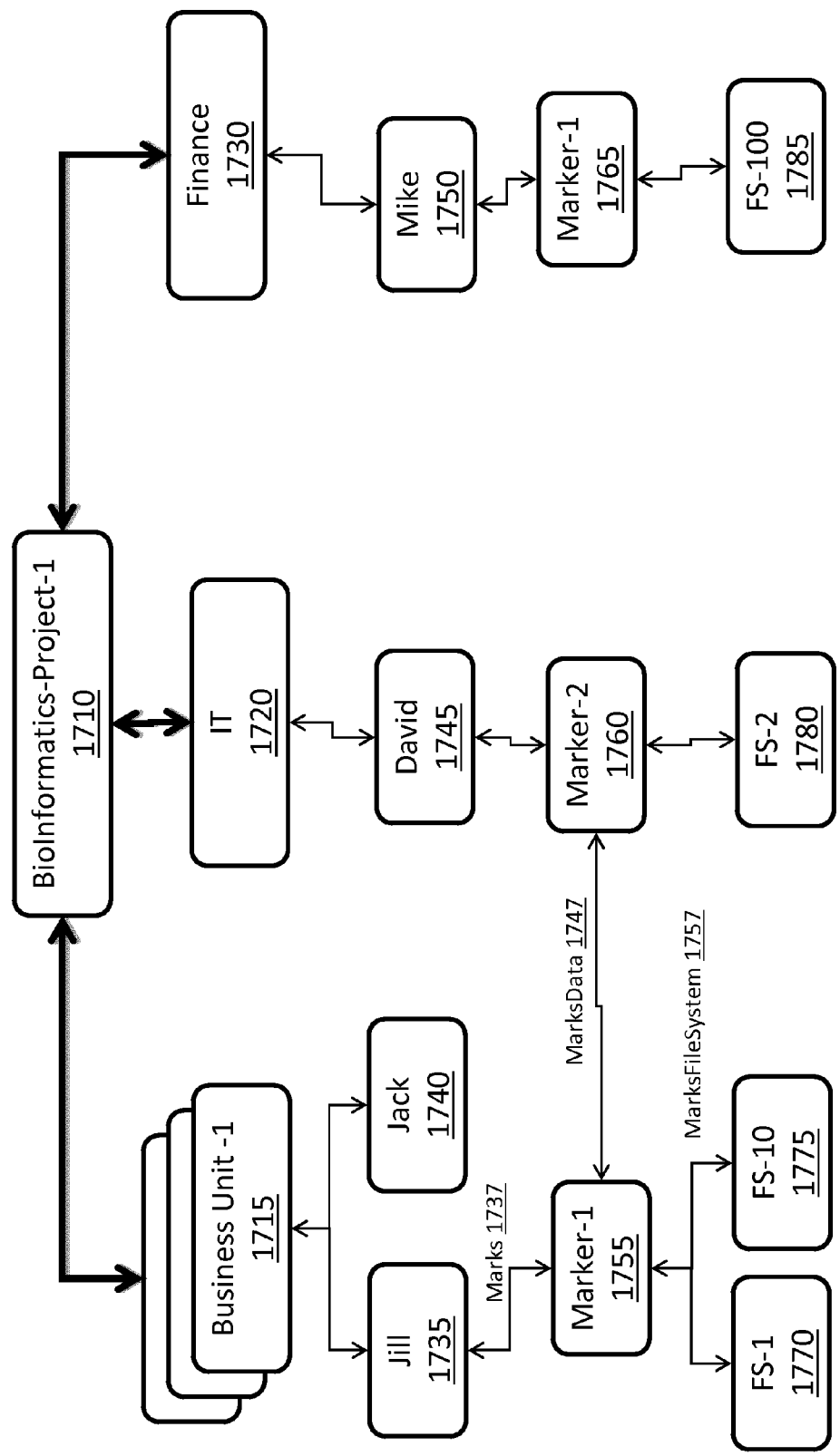
FIG. 17 is a simplified alternative illustration of a model representation of a marker view in a bioinformatics project, in accordance with an embodiment of the present disclosure.

Refer now to the example embodiment of FIG. 17. Bioinformatics project 1710 is composed of business unit 1715, IT 1720, and Finance 1730. Jack 1735 and Jill 1740 make up business unit 1715. David 1745 makes up IT 1720 and Mike 1750 makes up finance 1730. Maker 1755 marks Jill to marker 1 which marks files systems 1770 and 1775. Marker 1755 marks data to marker 1760, which marks file system 1780. Marker 1675 connects Mike 1750 to File system 1785.

Figure 18:
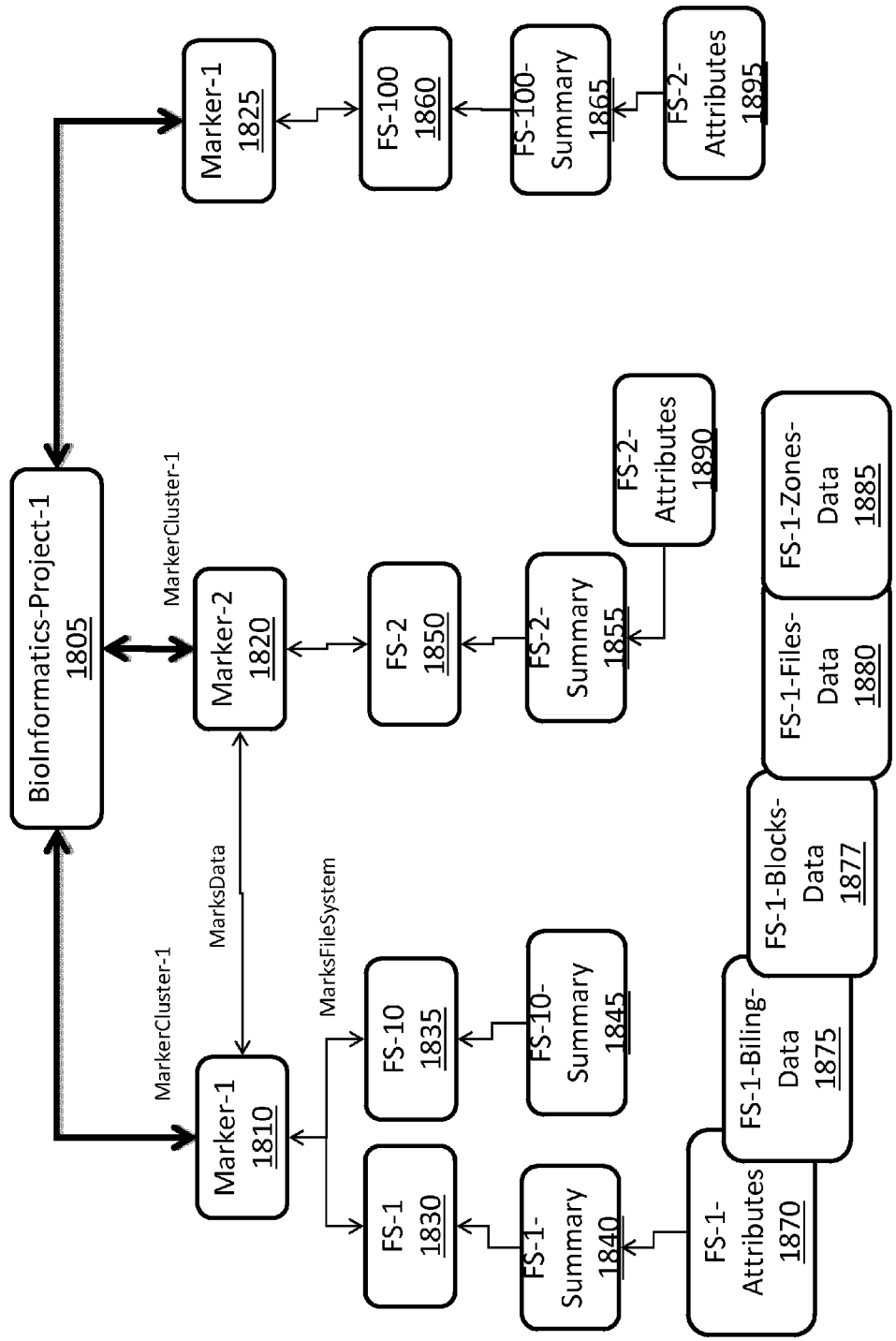
FIG. 18 is a simplified further illustration of a model representation of a marker view in a bioinformatics project, in accordance with an embodiment of the present disclosure.

Refer now to the example embodiment of FIG. 18. Bioinformatics project 1805 has marker 1810, marker 1820, and marker 1825. Marker 1810 marks File systems 1830 and 1835. File system 1830 has file system summary 1840 and file system 1835 has file system summary 1845. File system summary has attributes 1870, billing data 1875, block data 1877, files data 1880, and zones data 1885. Marker 1820 marks file system 1850 which has summary 1885. Summary 1885 has attributes 1890. Marker 1825 marks file system 1860. File system 1860 has file system summary 1865. File system summary 1865 has file system attributes 1895.

Figure 19:
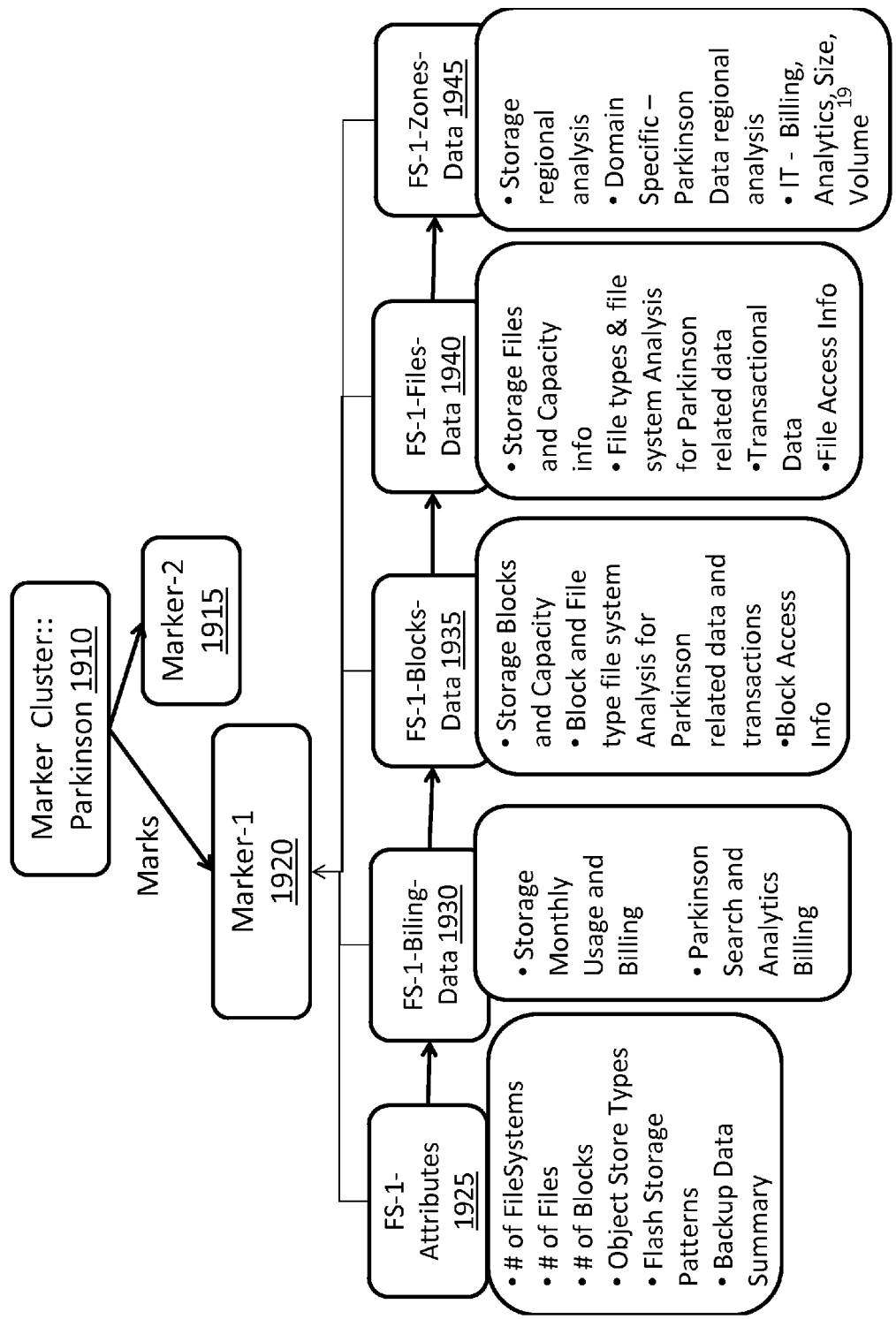
FIG. 19 is a simplified illustration of a model representation of an example marker view in a bioinformatics project, in accordance with an embodiment of the present disclosure.

Refer now to the example embodiment of FIG. 19 outlining a marker cluster for Parkinson's disease. Marker cluster 1910 has marker 1920 and marker 1915. Marker 1920 has file system attributes 1925, billing data 1930, blocks data 1935, file data 1940, and zones data 1945.

Genome Indexing

In certain embodiments, the current techniques may be used to generate an index or one or more index planes for Big Data information. In some embodiments, this index may be used to distribute the Big Data to nodes for analysis. In certain embodiments, the nodes may be those of a Hadoop type architecture. In further embodiments, several index planes may be generated. In still further embodiments, each index plane may be represented at a different level of abstraction and may created meshed planes of abstraction. In a particular embodiment, a plane of abstraction or index plan may be hierarchical. In other embodiments, the plane of abstraction may be cyclical. In most embodiments, the index plane or index planes may be used to distribute Big Data to the nodes. In further embodiments, map reduce algorithms may be applied to perform next generation sequencing analysis. In still further embodiments, the index plane may be a pre-reduce algorithm applied before a map-reduce algorithm to distribute Big data to processing nodes.

In some embodiments, the index plane may be used to aggregate and store information and analysis returned by the analysis nodes. In certain embodiments, the information in the index plane may be stored in a quickly accessible medium, which may enable requested information to be accessed by examining the information stored in the index plane instead of accessing the underlying data.

In some embodiments, techniques of the current disclosure may be applied to any indexing system. In certain embodiments, some of the techniques may be applied to the performance of in-memory analytics to create indices and to store indices. In further embodiments, the analytics may performed and stored at the index level In these embodiments, the actual indexed elements may reside in storage while the indexes may reside in-memory. In other embodiments, data may be brought from storage into main or quickly accessible memory based on number of indices pointing to the data. In some embodiments, the data may be stored in a low latency storage medium. In certain embodiments, the low latency storage medium may be flash ram or DRAM. In further embodiments, the low latency storage medium may enable a matrix type instant access mode for structured, unstructured and multi-structured data. In still further embodiments, the low latency storage medium may avoid cylindrical storage access times associated with a spinning storage medium.

In certain embodiments, the index planes may be located in a quickly accessible medium such as flash or DRAM. For example refer to the example embodiment to of FIG. 20. FIG. 20 illustrates some example metrics for different types of storage mediums. For example, the latency 2060 for DRAM 2010 is 0.005 microseconds. Conversely, the latency 2060 for HDD 2030 is 7-12 milliseconds. This chart illustrates several examples of how the use of different storage mediums can impact the access speed of information.

Figure 21:
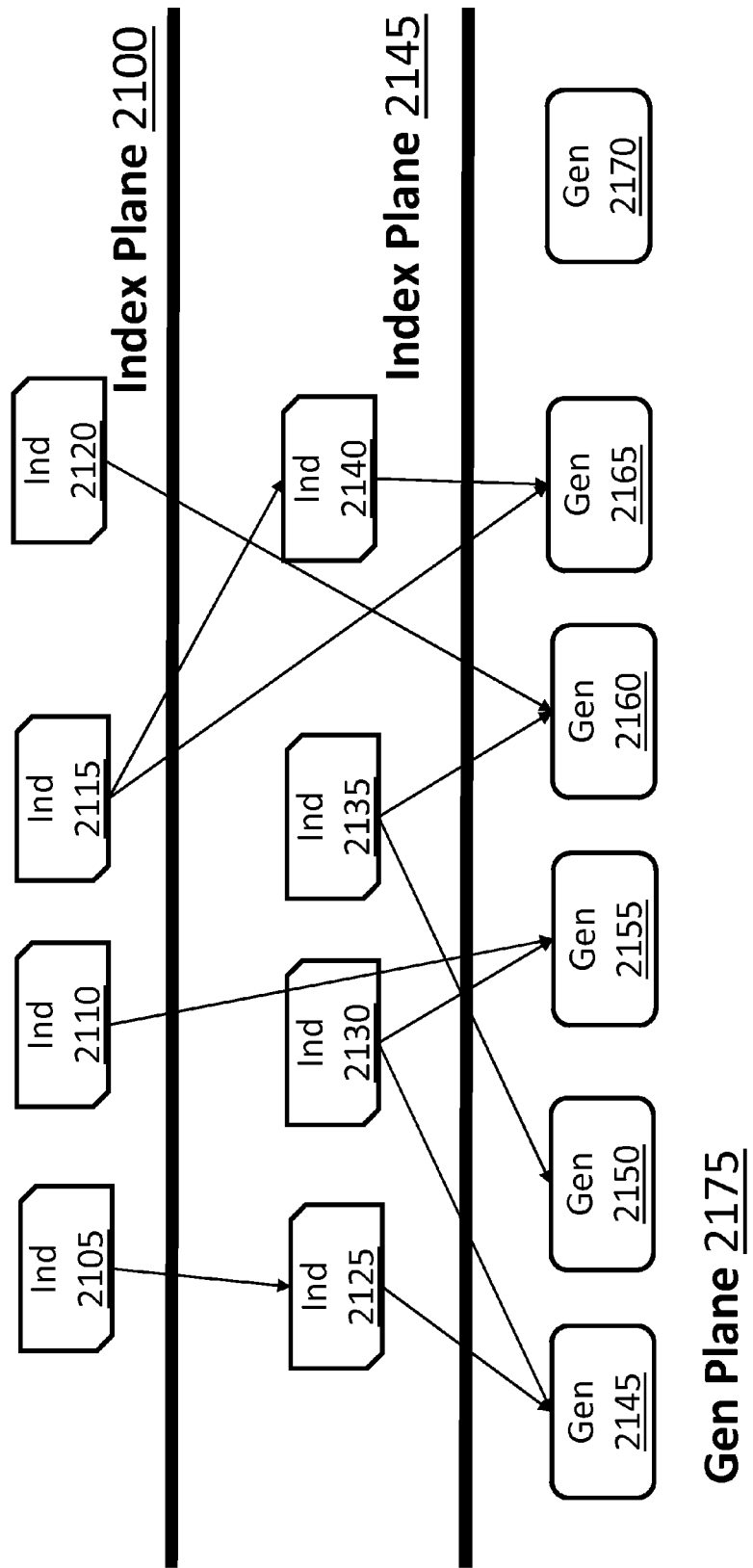
FIG. 21 is a simplified illustration of meshed planes of abstraction with two index planes and a generation plane, in accordance with an embodiment of the present disclosure.

Refer now to the example embodiment of FIG. 21. In this example embodiment, there are two index planes, 2120 and 2145, and a generation plane 2175. In this embodiment, the index planes map information onto the generation plane to enable information to be distributed to and computed by processing nodes. For example indices 2125 and 2130 may to generation 2145. Index 2105 maps to index 2125 and index 2110 maps to generation 2155.

Consider the example embodiment of FIG. 21 in reference to a Big Data set consisting of a set of genomic markers upon which analysis may be performed. In certain embodiments, there may be a set of sequences. In some embodiments, each sequence may be in a file and each sequence may be stored in a node. In some embodiments, the analysis may result in a sequence of indices in a format of keypairs upon which analysis can be performed. In some embodiments, it may be desired to understand what other sequences are 1-letter aligned at position1. In other embodiments, it may be desirable to determine what other sequences are 2-letter aligned at position1. In further embodiments, it may be desirable to determine what other sequences are 2-letter aligned at position2. In certain embodiments, the genome sequencing may be organized into key-value pairs. In some embodiments, the key may be a <letter-sequence,starting-position> pair and the value may be a Value=<SequenceId>. In other embodiments, several indices may be created such as one for 1-letter and another for 2-letter sub-sequence. In further embodiments, it may be desired to determine how may pairs have a particular combination, such as <C,1>. In other embodiments, it may be desired to query how many pairs have a <CA,1> pair.

Figure 22:
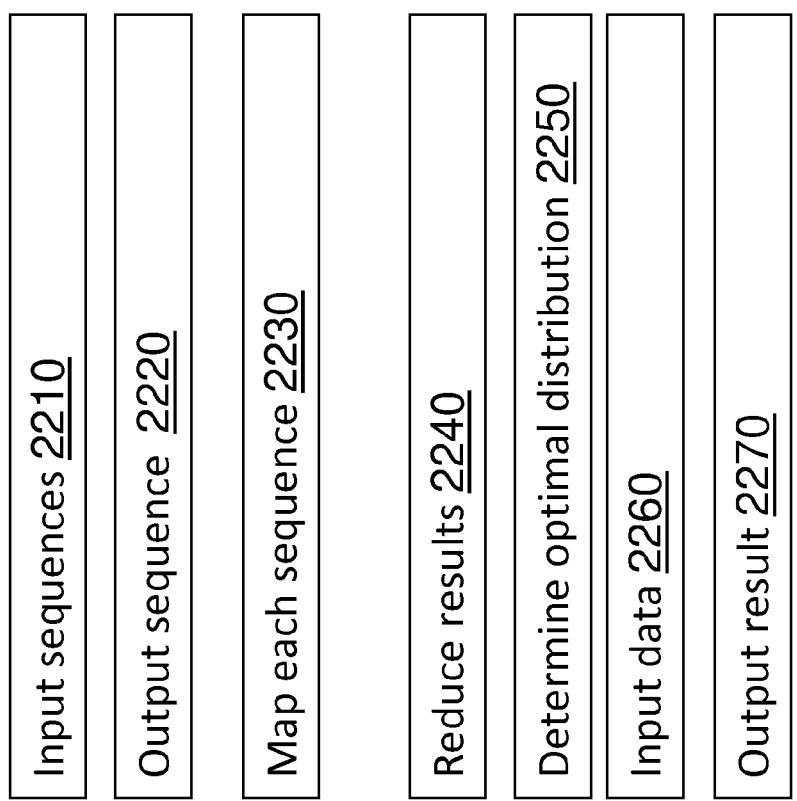
FIG. 22 is a simplified method for distributing and analyzing Big Data, in accordance with an embodiment of the present disclosure.

For example, refer to the example embodiment of FIG. 22. A collection of sequences may be inputted and each sequence may be in a file, and each file divided into segments, where each segment stored on a node (step 2210). A sequence of indexes in the format of key-value pairs may be outputted where a key is a <letter-sequence,starting-position> and a value is a <SequenceId> (step 2220). The extracted sub sequences may be mapped to create key-value pairs (step 2230). Duplicated in the data may be reduced (step 2340). An optimal way to distribute the data may be determined (step 2350). In certain embodiments the data may be replicated. The index data distributed across the nodes may be inputted (step 2360). The results of the query may be outputted (step 2370).

Figure 24:
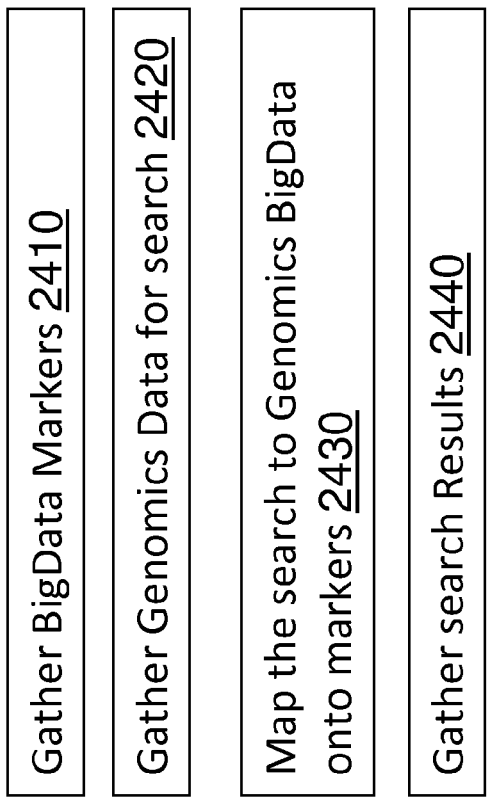
FIG. 24 is a simplified method for distributing and analyzing Big Data for BioInformatics, in accordance with an embodiment of the present disclosure.

Refer now to the example embodiments of FIGS. 23 and 24. The BioInformatics Big Data Storage may be started. The BioInformatics data markers, CAT 2320, GAT 2320, and TAC, 2340 may be gathered (step 2410). The genomics data for the search may be gathered (step 2420). The BigData search may be mapped on to markers (step 2430). The results of the mapping, such as shown in FIG. 23, may be gathered (step 2440).

Refer now to the example embodiment of FIG. 24. The genomics BigData and markers may be selected (step 2510). The genomics search patterns may be chosen gathered (step 2520). The marker indicates may be searched (step 2530). The Big Data set may be searched (step 2540). The search results may be reported (step 2550). The data consistency may be checked (Step 2560).

In certain embodiments, there may be different genome sequences of different length and makeup. In some embodiments, the sequences may be categorized into word sequences, sentence sequences, which may be a combination of word sequences, or in definite sequences which may be a set of indefinite sequences. In further embodiments, the set of word sequences may be indexed across several index planes. In certain embodiments, this information may be stored in an index construct. In further embodiments, the index construct may be stored in highly accessible low latency storage. In still further embodiments, the Big Data may be searched by accessing the index construct without accessing the underlying Big Data. In a particular embodiment, the example embodiment of FIG. 21 may represent index planes and the example embodiment of FIG. 23 may represent the index construct.

Figure 26:
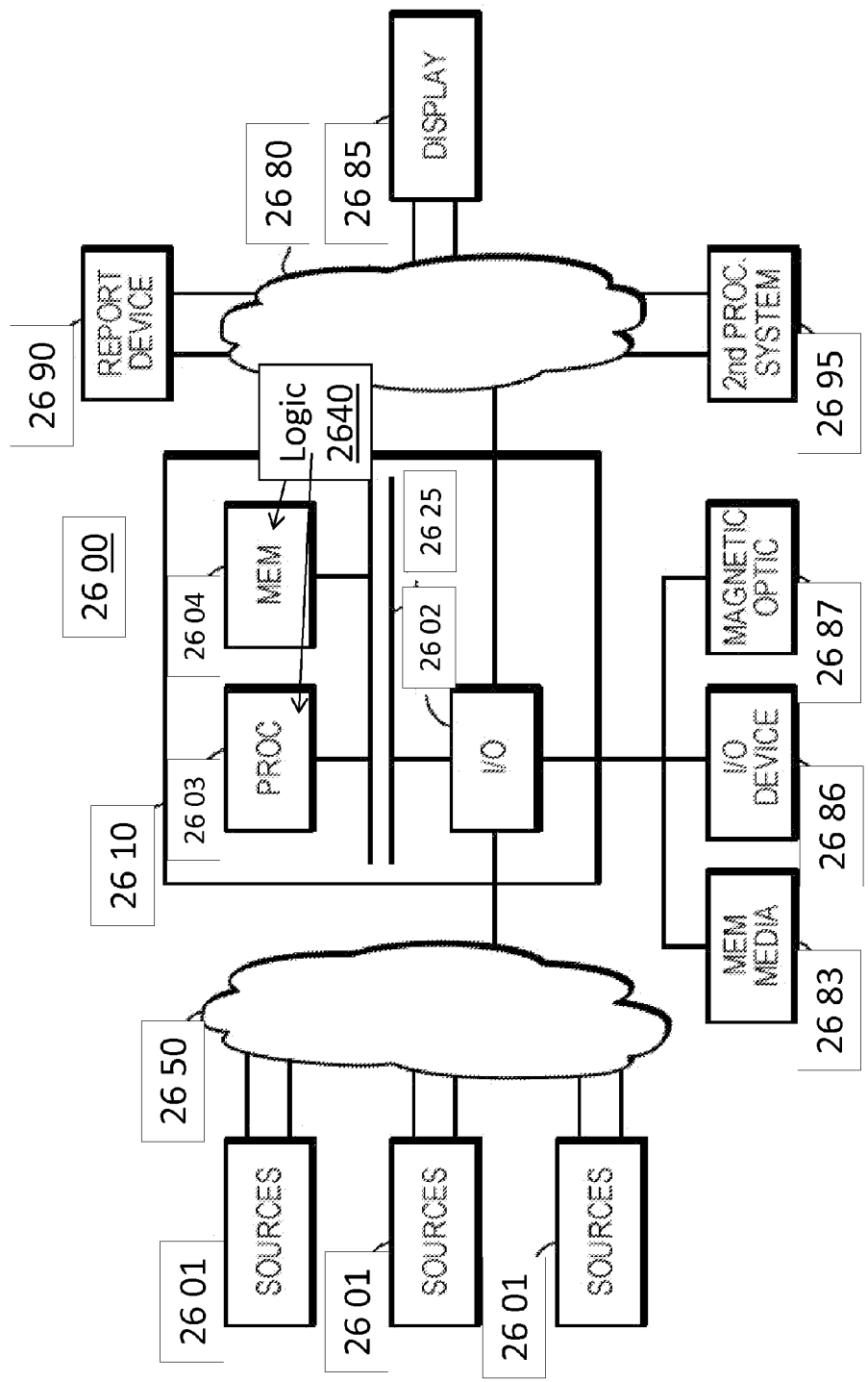
FIG. 26 is an example of an embodiment of an apparatus that may utilize the techniques described herein, in accordance with an embodiment of the present disclosure.
Figure 27:
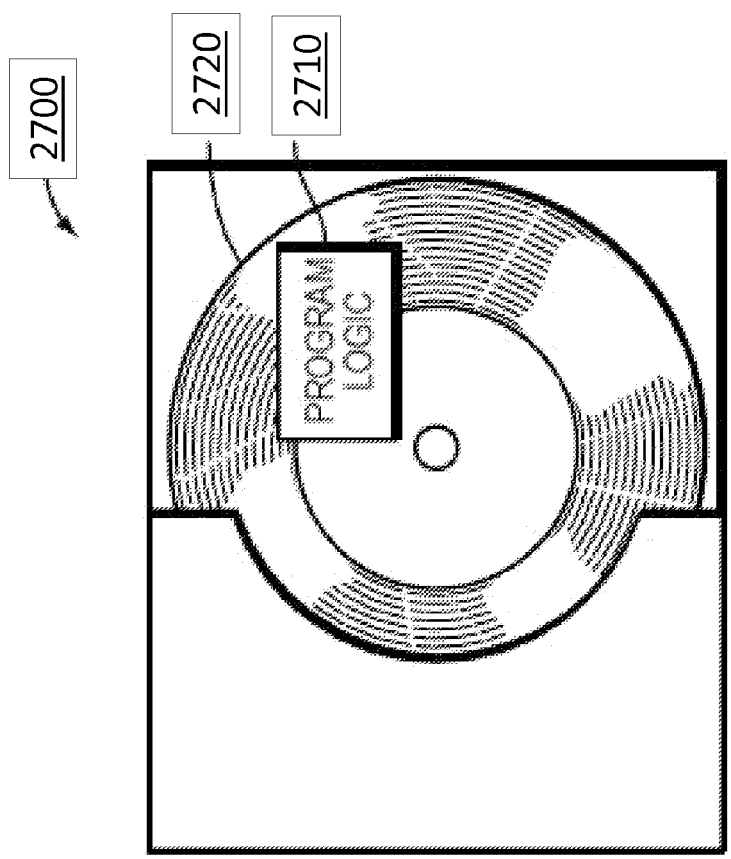
FIG. 27 is an example of an embodiment of a method embodied on a computer readable storage medium that may utilize the techniques described herein, in accordance with an embodiment of the present invention.

The methods and apparatus of this invention may take the form, at least partially, of program code (i.e., instructions) embodied in tangible media, such as floppy diskettes, CD-ROMs, hard drives, random access or read only-memory, or any other machine-readable storage medium. When the program code is loaded into and executed by a machine, such as the computer of FIG. 26, the machine becomes an apparatus for practicing the invention. When implemented on one or more general-purpose processors, the program code combines with such a processor 2603 to provide a unique apparatus that operates analogously to specific logic circuits. As such a general purpose digital machine can be transformed into a special purpose digital machine. FIG. 27 shows Program Logic 2734 embodied on a computer-readable medium 2730 as shown, and wherein the Logic is encoded in computer-executable code configured for carrying out the reservation service process of this invention and thereby forming a Computer Program Product 2700. The logic 2734 may be the same logic 2640 on memory 2604 loaded on processor 2603. The program logic may also be embodied in software modules, as modules, or as hardware modules.

Figure 25:
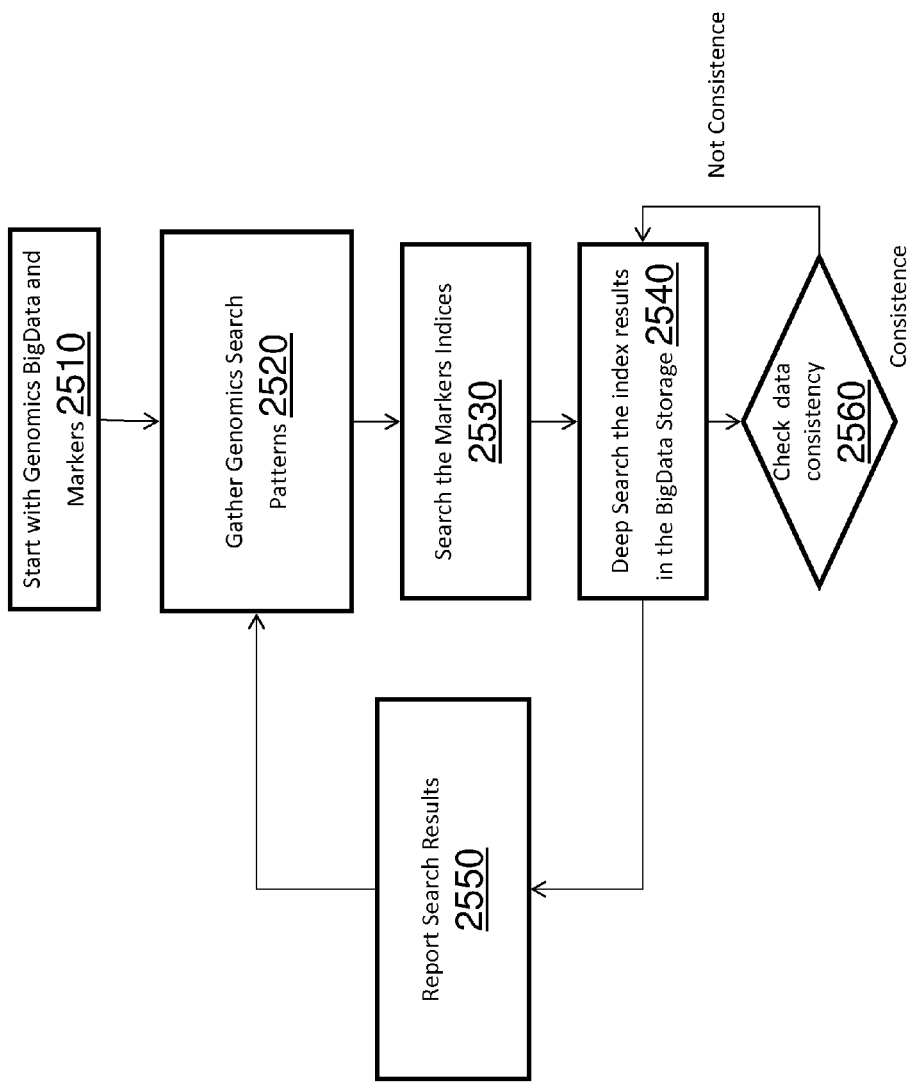
FIG. 25 is an alternative simplified method for distributing and analyzing Big Data for Bio Informatics, in accordance with an embodiment of the present disclosure.

The logic for carrying out the method may be embodied as part of the system described below, which is useful for carrying out a method described with reference to embodiments shown in, for example, FIG. 24 and FIG. 25. For purposes of illustrating the present invention, the invention is described as embodied in a specific configuration and using special logical arrangements, but one skilled in the art will appreciate that the device is not limited to the specific configuration but rather only by the claims included with this specification.

Although the foregoing invention has been described in some detail for purposes of clarity of understanding, it will be apparent that certain changes and modifications may be practiced within the scope of the appended claims. Accordingly, the present implementations are to be considered as illustrative and not restrictive, and the invention is not to be limited to the details given herein, but may be modified within the scope and equivalents of the appended claims.

What is claimed is:

1. A computer implemented method for modeling a Big Data dataset, the method comprising:
    creating non-specific representations of the Big Data dataset by representing, as objects in a computer model, the non-specific representations including metaInformation, DataSet, BigData and Properties representations; wherein respective portions of the BigData dataset are enabled to be stored in respective file systems and object stores;
    creating non-specific representations of indices, wherein the indices are mapped to one or more key-value pairs; wherein the non-specific representation of indices are used to create one or more index planes enabled to reference portions of the Big Data dataset; wherein the respective portions are stored in the respective file systems and object stores; wherein each of the one or more index planes represents the Big Data dataset at a different level of abstraction; wherein each of the one or more index planes is enabled to be a part of a meshed plane of abstraction; wherein analytics are enabled to be performed and stored at each of the one or more index planes; wherein a first index plane of the one or more index planes and a second index plane of the one or more index planes are enabled to be combined at a generation plane; and
    enabling the Big Data dataset to be distributed to nodes based on the mapping of the one or more index planes; wherein each node of the nodes is enabled to be part of a respective file system or object store to enable the Big Data dataset to be stored across the respective file systems and object stores; wherein the mapping of the one or more index planes enables the Big Data dataset to be viewed irrespective of underlying file systems and object stores.

2. The method of claim 1 wherein a key is a <letter-sequence,starting-position> and a value is a <SequenceId>.

3. The method of claim 1 further comprising:
    representing a set of markers for the BigData; and
    mapping the BigData to the set of markers.

4. The method of claim 3 further comprising:
    determining an optimal distribution to the markers based on the mapping.

5. The method of claim 4 further comprising:
    distributing the BigData based on the mapping to a set of processing nodes.

6. The method of claim 1 wherein the indices are mapped to a set of index planes, wherein one member of the set of index planes is an abstract plane.

7. A computer program product for use in replication comprising:
    a non-transitory computer readable medium encoded with computer executable program code for migration of data, the code configured to enable the execution of:
    creating non-specific representations of the Big Data dataset by representing, as objects in a computer model, the non-specific representations including metaInformation, DataSet, BigData and Properties representations; wherein respective portions of the BigData dataset are enabled to be stored in respective file systems and object stores;
    creating non-specific representations of indices, wherein the indices are mapped to one or more key-value pairs; wherein the non-specific representation of indices are used to create one or more index planes enabled to reference portions of the Big Data dataset; wherein the respective portions are stored in the respective file systems and object stores; wherein each of the one or more index planes represents the Big Data dataset at a different level of abstraction; wherein each of the one or more index planes is enabled to be a part of a meshed plane of abstraction; wherein analytics are enabled to be performed and stored at each of the one or more index planes; wherein a first index plane of the one or more index planes and a second index plane of the one or more index planes are enabled to be combined at a generation plane; and
    enabling the Big Data dataset to be distributed to nodes based on the mapping of the one or more index planes; wherein each node of the nodes is enabled to be part of a respective file system or object store to enable the Big Data dataset to be stored across the respective file systems and object stores; wherein the mapping of the one or more index planes enables the Big Data dataset to be viewed irrespective of underlying file systems and object stores.

8. The program product of claim 7 wherein a key is a <letter-sequence,starting-position> and a value is a <SequenceId>.

9. The program product of claim 7 wherein the executable program code is further configured for execution of:
    representing a set of markers for the BigData; and
    mapping the BigData to the set of markers.

10. The program product of claim 9 wherein the executable program code is further configured for execution of:
    determining an optimal distribution to the markers based on the mapping.

11. The program product of claim 10 wherein the executable program code is further configured for execution of:
    distributing the BigData based on the mapping to a set of processing nodes.

12. The program product of claim 8 wherein the indices are mapped to a set of index planes, wherein one member of the set of index planes is an abstract plane.

13. A system, comprising:
    a data storage system; and
    computer-executable logic encoded in memory of one or more computers in communication with the data storage system for modeling a big dataset, wherein the computer-executable logic is configured for the execution of:
    creating non-specific representations of the Big Data dataset by representing, as objects in a computer model in one or more processors, non-specific representations including metaInformation, DataSet, BigData and Properties representations; wherein respective portions of the BigData dataset are enabled to be stored in respective file systems and object stores;

creating non-specific representations of indices, wherein the indices are mapped to one or more key-value pairs; wherein the non-specific representation of indices are used to create one or more index planes enabled to reference portions of the Big Data dataset; wherein the respective portions are stored in the respective file systems and object stores; wherein each of the one or more index planes represents the Big Data dataset at a different level of abstraction; wherein each of the one or more index planes is enabled to be a part of a meshed plane of abstraction; wherein analytics are enabled to be performed and stored at each of the one or more index planes; wherein a first index plane of the one or more index planes and a second index plane of the one or more index planes are enabled to be combined at a generation plane; and enabling the Big Data dataset to be distributed to nodes based on the mapping of the one or more index planes; wherein each node of the nodes is enabled to be part of a respective file system or object store to enable the Big Data dataset to be stored across the respective file systems and object stores; wherein the mapping of the one or more index planes enables the Big Data dataset to be viewed irrespective of underlying file systems and object stores.

14. The system of claim 13 wherein a key is a <letter-sequence,starting-position> and a value is a <SequenceId>.

15. The system of claim 13, wherein the computer-executable logic is further configured for the execution of:

representing a set of markers for the BigData; and mapping of the BigData to the set of markers.

16. The system of claim 13, wherein the computer-executable logic is further configured for the execution of:

enabling determination of an optimal distribution to the markers based on the mapping.

17. The system of claim 13, wherein the computer-executable logic is further configured for the execution of:

enabling distributing the BigData based on the mapping to a set of processing nodes.

18. The system of claim 13 wherein the indices are mapped to a set of index planes, wherein one member of the set of index planes is an abstract plane.

19. The system of claim 15, wherein the computer-executable logic is further configured for the execution of:

enabling creation of non-specific representations of marker clusters, as objects in a computer model; and enabling creation of non-specific representations of marks, as objects in a computer model, as non-specific representations comprising administration properties, contextual properties, and semantical properties.

20. The method of claim 1 wherein the nodes are enabled to perform analysis on a portion of the Big Data dataset distributed according to the one or more index planes.

21. The method of claim 20 wherein the index planes enable aggregation and storing of analysis performed by the nodes.

* * * * *